(12) United States Patent
Kim et al.

(10) Patent No.: US 9,975,933 B2
(45) Date of Patent: May 22, 2018

(54) TUMOR TISSUE-PENETRATING PEPTIDE SPECIFIC TO NEUROPILIN AND FUSION PROTEIN HAVING SAME PEPTIDE FUSED THEREIN

(71) Applicant: AJOU UNIVERSITY INDUSTRY-ACADEMIC COOPERATION FOUNDATION, Suwon-si, Gyeonggi-do (KR)

(72) Inventors: Yong Sung Kim, Suwon-si (KR); Tae Hwan Shin, Daegu (KR); Yae Jin Kim, Busan (KR); Eun Sil Sung, Suwon-si (KR)

(73) Assignee: AJOU UNIVERSITY INDUSTRY-ACADEMIC COOPERATION FOUNDATION, Suwon-si, Gyeonggi-do (KR)

( * ) Notice: Subject to any disclaimer, the term of this patent is extended or adjusted under 35 U.S.C. 154(b) by 115 days.

(21) Appl. No.: 14/893,317

(22) PCT Filed: May 22, 2014

(86) PCT No.: PCT/KR2014/004571
§ 371 (c)(1),
(2) Date: Nov. 23, 2015

(87) PCT Pub. No.: WO2014/189303
PCT Pub. Date: Nov. 27, 2014

(65) Prior Publication Data
US 2016/0130315 A1    May 12, 2016

(30) Foreign Application Priority Data

May 23, 2013   (KR) ........................ 10-2013-0058619

(51) Int. Cl.
*C07K 14/47* (2006.01)
*A61K 38/00* (2006.01)

(52) U.S. Cl.
CPC .......... *C07K 14/4703* (2013.01); *A61K 38/00* (2013.01); *C07K 2319/00* (2013.01); *C07K 2319/02* (2013.01); *C07K 2319/30* (2013.01)

(58) Field of Classification Search
None
See application file for complete search history.

(56) References Cited

U.S. PATENT DOCUMENTS

| 5,639,856 A | * | 6/1997 | Goodman | .......... | A01K 67/0339 530/326 |
| 5,935,865 A | * | 8/1999 | Goodman | .......... | A01K 67/0339 436/501 |
| 6,013,781 A | * | 1/2000 | Goodman | .......... | A01K 67/0339 536/23.1 |
| 6,936,450 B2 | * | 8/2005 | Levine | ..................... | C12N 9/12 424/94.6 |
| 7,485,414 B2 | * | 2/2009 | Lorens | ............... | C07K 14/4702 435/325 |
| 7,601,692 B2 | * | 10/2009 | Levine | ................. | C07K 14/523 514/1.1 |
| 7,745,391 B2 | * | 6/2010 | Mintz | ..................... | G06F 19/24 514/19.3 |

FOREIGN PATENT DOCUMENTS

| WO | WO 01/38491 | * | 5/2001 | |
| WO | WO 01/57273 | * | 8/2001 | ............... C12Q 1/68 |

* cited by examiner

*Primary Examiner* — Amber D Steele
(74) *Attorney, Agent, or Firm* — Vorys, Sater, Seymour and Pease LLP; Mih Suhn Koh

(57) ABSTRACT

A tumor tissue-penetrating peptide specifically binding to neuropilin, or a fusion protein, a small molecule drug, a nanoparticle, or a liposome having the peptide fused therein is provided, as well as a method for preparing the same and a pharmaceutical composition comprising the same for treating, diagnosing, or preventing cancer or angiogenesis-related diseases. The tumor tissue-penetrating peptide is fused to the C-terminus of an anticancer antibody heavy-chain constant region (Fc) and the fused antibody specifically binds to neuropilin, and specifically accumulates in tumor tissue, widens intercellular gaps between tumor vascular endothelial cells, promotes extravasation, increases infiltration within tumor tissue, and shows a remarkably increased in vivo tumor-suppressing activity. Furthermore, the tumor tissue-penetrating peptide is fused into a fusion protein and inhibits the angiogenic function of neuropilin coreceptors resulting from targeting of neuropilin, and is expected to have an alleviating effect on angiogenesis-related diseases.

29 Claims, 19 Drawing Sheets

PDZ BD (A)

(B)

(A)

(B)

PPC-1

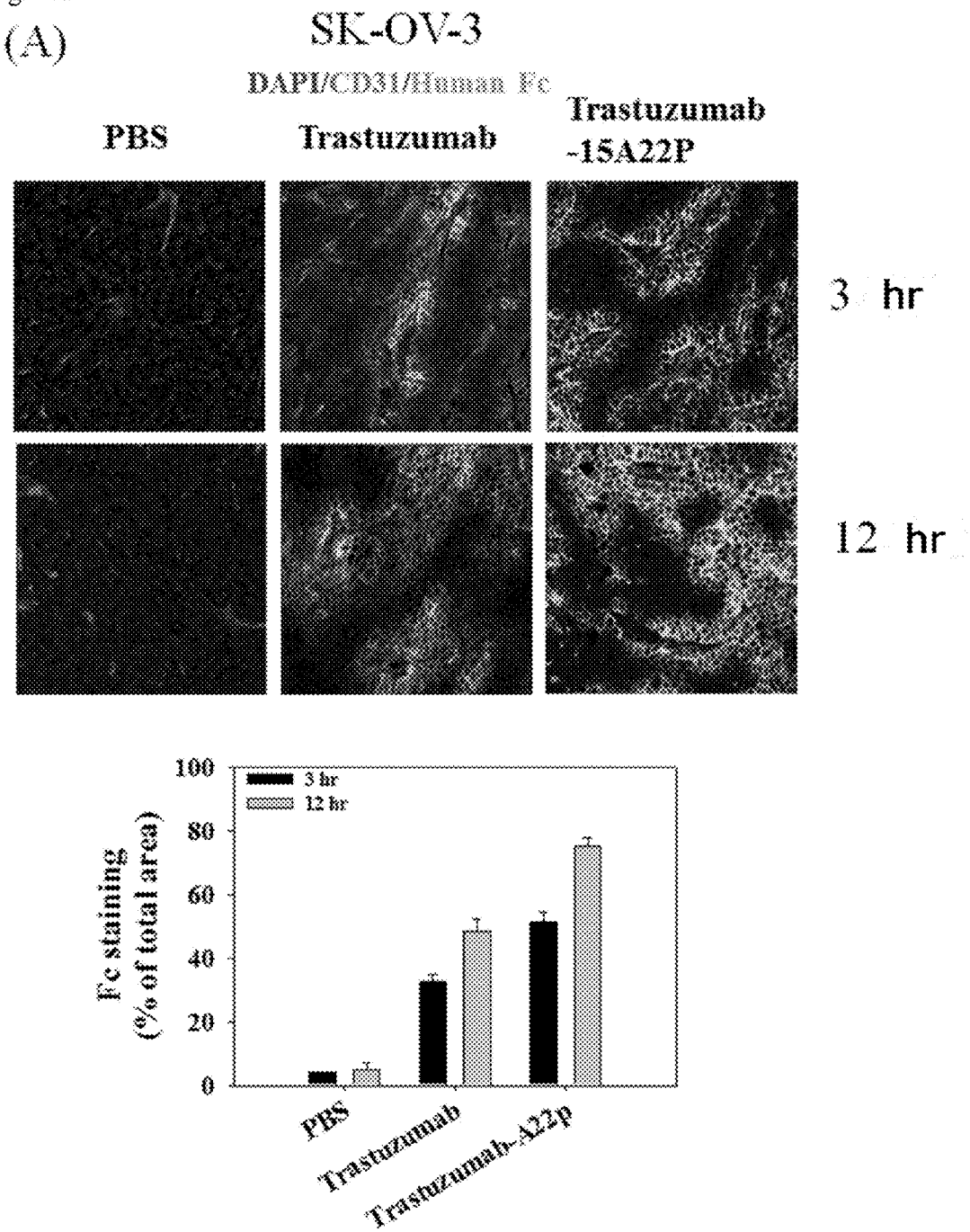

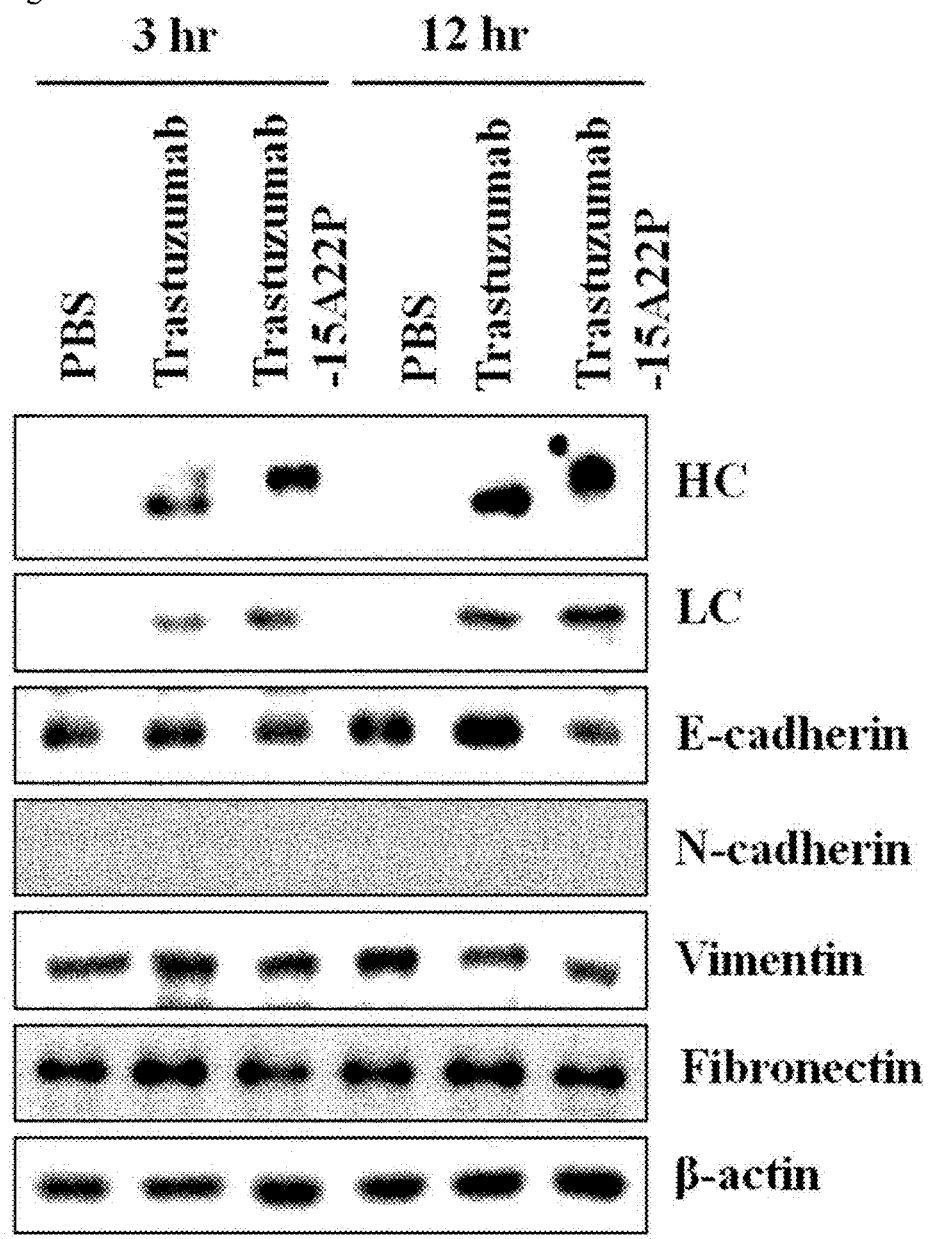

SEQUENCE LISTING

```
<160> NUMBER OF SEQ ID NOS: 23

<210> SEQ ID NO 1
<211> LENGTH: 22
<212> TYPE: PRT
<213> ORGANISM: Artificial Sequence
<220> FEATURE:
<223> OTHER INFORMATION: A22

<400> SEQUENCE: 1

His Thr Pro Gly Asn Ser Asn Lys Trp Lys His Leu Gln Glu Asn Lys
  1               5                  10                  15

Lys Gly Arg Asn Arg Arg
            20

<210> SEQ ID NO 2
<211> LENGTH: 22
```

```
<212> TYPE: PRT
<213> ORGANISM: Artificial Sequence
<220> FEATURE:
<223> OTHER INFORMATION: A22p

<400> SEQUENCE: 2

His Thr Pro Gly Asn Ser Asn Lys Trp Lys His Leu Gln Glu Asn Lys
 1               5                  10                  15

Lys Gly Arg Pro Arg Arg
            20

<210> SEQ ID NO 3
<211> LENGTH: 22
<212> TYPE: PRT
<213> ORGANISM: Artificial Sequence
<220> FEATURE:
<223> OTHER INFORMATION: F22

<400> SEQUENCE: 3

Arg Glu Ala Pro Gly Ala Pro Arg Ser Pro Glu Pro Gln Asp Gln Lys
 1               5                  10                  15

Lys Pro Arg Asn Arg Arg
            20

<210> SEQ ID NO 4
<211> LENGTH: 22
<212> TYPE: PRT
<213> ORGANISM: Artificial Sequence
<220> FEATURE:
<223> OTHER INFORMATION: F22p

<400> SEQUENCE: 4

Arg Glu Ala Pro Gly Ala Pro Arg Ser Pro Glu Pro Gln Asp Gln Lys
 1               5                  10                  15

Lys Pro Arg Pro Arg Arg
            20

<210> SEQ ID NO 5
<211> LENGTH: 26
<212> TYPE: PRT
<213> ORGANISM: Artificial Sequence
<220> FEATURE:
<223> OTHER INFORMATION: 4A22

<400> SEQUENCE: 5

Gly Ala Gly Ala His Thr Pro Gly Asn Ser Asn Lys Trp Lys His Leu
 1               5                  10                  15

Gln Glu Asn Lys Lys Gly Arg Asn Arg Arg
            20                  25

<210> SEQ ID NO 6
<211> LENGTH: 37
<212> TYPE: PRT
<213> ORGANISM: Artificial Sequence
<220> FEATURE:
<223> OTHER INFORMATION: 15A22

<400> SEQUENCE: 6

Gly Gly Gly Gly Ser Gly Gly Gly Gly Ser Gly Gly Gly Gly Ser His
 1               5                  10                  15

Thr Pro Gly Asn Ser Asn Lys Trp Lys His Leu Gln Glu Asn Lys Lys
                20                  25                  30

Gly Arg Asn Arg Arg
         35
```

<210> SEQ ID NO 7
<211> LENGTH: 37
<212> TYPE: PRT
<213> ORGANISM: Artificial Sequence
<220> FEATURE:
<223> OTHER INFORMATION: 15A22p

<400> SEQUENCE: 7

Gly Gly Gly Gly Ser Gly Gly Gly Gly Ser Gly Gly Gly Gly Ser His
 1               5                  10                  15

Thr Pro Gly Asn Ser Asn Lys Trp Lys His Leu Gln Glu Asn Lys Lys
            20                  25                  30

Gly Arg Pro Arg Arg
        35

<210> SEQ ID NO 8
<211> LENGTH: 26
<212> TYPE: PRT
<213> ORGANISM: Artificial Sequence
<220> FEATURE:
<223> OTHER INFORMATION: 4F22

<400> SEQUENCE: 8

Gly Ala Gly Ala Arg Glu Ala Pro Gly Ala Pro Arg Ser Pro Glu Pro
 1               5                  10                  15

Gln Asp Gln Lys Lys Pro Arg Asn Arg Arg
            20                  25

<210> SEQ ID NO 9
<211> LENGTH: 37
<212> TYPE: PRT
<213> ORGANISM: Artificial Sequence
<220> FEATURE:
<223> OTHER INFORMATION: 15F22

<400> SEQUENCE: 9

Gly Gly Gly Gly Ser Gly Gly Gly Gly Ser Gly Gly Gly Gly Ser Arg
 1               5                  10                  15

Glu Ala Pro Gly Ala Pro Arg Ser Pro Glu Pro Gln Asp Gln Lys Lys
            20                  25                  30

Pro Arg Asn Arg Arg
        35

<210> SEQ ID NO 10
<211> LENGTH: 37
<212> TYPE: PRT
<213> ORGANISM: Artificial Sequence
<220> FEATURE:
<223> OTHER INFORMATION: 15F22p

<400> SEQUENCE: 10

Gly Gly Gly Gly Ser Gly Gly Gly Gly Ser Gly Gly Gly Gly Ser Arg
 1               5                  10                  15

Glu Ala Pro Gly Ala Pro Arg Ser Pro Glu Pro Gln Asp Gln Lys Lys
            20                  25                  30

Pro Arg Pro Arg Arg
        35

<210> SEQ ID NO 11
<211> LENGTH: 40
<212> TYPE: PRT
<213> ORGANISM: Artificial Sequence

```
<220> FEATURE:
<223> OTHER INFORMATION: linker
<220> FEATURE:
<221> NAME/KEY: misc_feature
<222> LOCATION: (1)..(38)
<223> OTHER INFORMATION: these nucleotides may be absent

<400> SEQUENCE: 11

Gly Ala Gly Ala Gly Ala Gly Ala Gly Ala Gly Ala Gly Ala Gly Ala
  1               5                  10                  15

Gly Ala Gly Ala Gly Ala Gly Ala Gly Ala Gly Ala Gly Ala Gly Ala
                 20                  25                  30

Gly Ala Gly Ala Gly Ala Gly Ala
             35                  40

<210> SEQ ID NO 12
<211> LENGTH: 100
<212> TYPE: PRT
<213> ORGANISM: Artificial Sequence
<220> FEATURE:
<223> OTHER INFORMATION: linker

<400> SEQUENCE: 12

Gly Gly Gly Gly Ser Gly Gly Gly Gly Ser Gly Gly Gly Gly Ser Gly
  1               5                  10                  15

Gly Gly Gly Ser Gly Gly Gly Gly Ser Gly Gly Gly Gly Ser Gly Gly
                 20                  25                  30

Gly Gly Ser Gly Gly Gly Gly Ser Gly Gly Gly Gly Ser Gly Gly Gly
             35                  40                  45

Gly Ser Gly Gly Gly Gly Ser Gly Gly Gly Gly Ser Gly Gly Gly Gly
         50                  55                  60

Ser Gly Gly Gly Gly Ser Gly Gly Gly Gly Ser Gly Gly Gly Gly Ser
 65                  70                  75                  80

Gly Gly Gly Gly Ser Gly Gly Gly Gly Ser Gly Gly Gly Gly Ser Gly
                 85                  90                  95

Gly Gly Gly Ser
            100

<210> SEQ ID NO 13
<211> LENGTH: 4
<212> TYPE: PRT
<213> ORGANISM: Artificial Sequence
<220> FEATURE:
<223> OTHER INFORMATION: site recognizing furin hydrolysis enzymes
<220> FEATURE:
<221> NAME/KEY: MISC_FEATURE
<222> LOCATION: (2)
<223> OTHER INFORMATION: any naturally-occurring amino acid

<400> SEQUENCE: 13

Arg Xaa Arg Arg
  1

<210> SEQ ID NO 14
<211> LENGTH: 26
<212> TYPE: PRT
<213> ORGANISM: Artificial Sequence
<220> FEATURE:
<223> OTHER INFORMATION: Sema3G

<400> SEQUENCE: 14

Cys Phe Arg Ser Arg Ser Arg Gly Lys Gln Ala Arg Gly Lys Ser Trp
  1               5                  10                  15
```

```
Ala Gly Leu Glu Leu Gly Lys Lys Met Lys
            20                  25
```

<210> SEQ ID NO 15
<211> LENGTH: 38
<212> TYPE: PRT
<213> ORGANISM: Artificial Sequence
<220> FEATURE:
<223> OTHER INFORMATION: Sema3A

<400> SEQUENCE: 15

```
Glu Gln Val Trp Lys Arg Asp Arg Lys Gln Arg Arg Gln Arg Pro Gly
 1               5                  10                  15

His Thr Pro Gly Asn Ser Asn Lys Trp Lys His Leu Gln Glu Asn Lys
            20                  25                  30

Lys Gly Arg Asn Arg Arg
        35
```

<210> SEQ ID NO 16
<211> LENGTH: 21
<212> TYPE: PRT
<213> ORGANISM: Artificial Sequence
<220> FEATURE:
<223> OTHER INFORMATION: Sema3B

<400> SEQUENCE: 16

```
Arg Pro Gln Pro Ala Leu Gln Ser Leu Pro Leu Glu Ser Arg Arg Lys
 1               5                  10                  15

Gly Arg Asn Arg Arg
            20
```

<210> SEQ ID NO 17
<211> LENGTH: 36
<212> TYPE: PRT
<213> ORGANISM: Artificial Sequence
<220> FEATURE:
<223> OTHER INFORMATION: Sema3C

<400> SEQUENCE: 17

```
Lys Asp Thr Arg Gln Gln His Gln Gln Gly Asp Glu Ser Gln Lys Met
 1               5                  10                  15

Arg Gly Asp Tyr Gly Lys Leu Lys Ala Leu Ile Asn Ser Arg Lys Ser
            20                  25                  30

Arg Asn Arg Arg
        35
```

<210> SEQ ID NO 18
<211> LENGTH: 32
<212> TYPE: PRT
<213> ORGANISM: Artificial Sequence
<220> FEATURE:
<223> OTHER INFORMATION: Sema3D

<400> SEQUENCE: 18

```
Glu Gln Met Trp His Arg Glu Lys Arg Arg Gln Arg Asn Lys Gly Gly
 1               5                  10                  15

Pro Lys Trp Lys His Met Gln Glu Met Lys Lys Lys Arg Asn Arg Arg
            20                  25                  30
```

<210> SEQ ID NO 19
<211> LENGTH: 36
<212> TYPE: PRT
<213> ORGANISM: Artificial Sequence
<220> FEATURE:

<223> OTHER INFORMATION: Sema3E

<400> SEQUENCE: 19

Thr Asp Arg Lys Arg Lys Lys Leu Lys Met Ser Pro Ser Lys Trp Lys
 1               5                  10                  15

Tyr Ala Asn Pro Gln Glu Lys Lys Leu Arg Ser Lys Pro Glu His Tyr
             20                  25                  30

Arg Leu Pro Arg
         35

<210> SEQ ID NO 20
<211> LENGTH: 33
<212> TYPE: PRT
<213> ORGANISM: Artificial Sequence
<220> FEATURE:
<223> OTHER INFORMATION: Sema3F

<400> SEQUENCE: 20

Gln Gly Tyr Trp Arg His Val Pro Pro Ser Pro Arg Glu Ala Pro Gly
 1               5                  10                  15

Ala Pro Arg Ser Pro Glu Pro Gln Asp Gln Lys Lys Pro Arg Asn Arg
             20                  25                  30

Arg

<210> SEQ ID NO 21
<211> LENGTH: 55
<212> TYPE: PRT
<213> ORGANISM: Artificial Sequence
<220> FEATURE:
<223> OTHER INFORMATION: VEGF165

<400> SEQUENCE: 21

Ala Arg Gln Glu Asn Pro Cys Gly Pro Cys Ser Glu Arg Arg Lys His
 1               5                  10                  15

Leu Phe Val Gln Asp Pro Gln Thr Cys Lys Cys Ser Cys Lys Asn Thr
             20                  25                  30

Asp Ser Arg Cys Lys Ala Arg Gln Leu Glu Leu Asn Glu Arg Thr Cys
         35                  40                  45

Arg Cys Asp Lys Pro Arg Arg
     50                  55

<210> SEQ ID NO 22
<211> LENGTH: 35
<212> TYPE: PRT
<213> ORGANISM: Artificial Sequence
<220> FEATURE:
<223> OTHER INFORMATION: VEGF145

<400> SEQUENCE: 22

Ala Arg Gln Glu Lys Lys Ser Val Arg Gly Lys Gly Lys Gly Gln Lys
 1               5                  10                  15

Arg Lys Arg Lys Lys Ser Arg Tyr Lys Ser Trp Ser Val Cys Asp Lys
             20                  25                  30

Pro Arg Arg
         35

<210> SEQ ID NO 23
<211> LENGTH: 11
<212> TYPE: PRT

```
<213> ORGANISM: Artificial Sequence
<220> FEATURE:
<223> OTHER INFORMATION: VEGF121

<400> SEQUENCE: 23

Ala Arg Gln Glu Lys Cys Asp Lys Pro Arg Arg
 1               5                  10
```

TUMOR TISSUE-PENETRATING PEPTIDE SPECIFIC TO NEUROPILIN AND FUSION PROTEIN HAVING SAME PEPTIDE FUSED THEREIN

SEQUENCE LISTING

The Sequence Listing submitted in text format (.txt) filed on Dec. 12, 2017, named "SequenceListing.txt", created on Dec. 12, 2017 (9.07 KB), is incorporated herein by reference.

TECHNICAL FIELD

The present invention relates to a tumor tissue-penetrating peptide (TPP) specifically binding to neuropilin.

Also, the present invention relates to a fusion protein, a small molecule drug, a nanoparticle, or a liposome having the tumor tissue-penetrating peptide fused therein.

Also, the present invention relates to a polynucleotide coding the tumor tissue-penetrating peptide, a recombinant vector including the same, a host cell transformed with this vector, and a method for preparing a tumor tissue-penetrating peptide using the host cell.

Also, the present invention relates to a pharmaceutical composition for treating or preventing cancer, including the tumor tissue-penetrating peptide, or a fusion protein, a small molecule drug, a nanoparticle, or a liposome having the peptide fused therein.

Also, the present invention relates to a composition for diagnosing cancer, including the tumor tissue-penetrating peptide, or a fusion protein, a small molecule drug, a nanoparticle, or a liposome having the peptide fused therein.

BACKGROUND ART

In the development research of antibodies for treatment, a hybridoma technology capable of producing monoclonal antibodies was developed about 35 years ago. Additionally, chimeric/humanized antibodies overcoming immunogenicity of mouse antibodies (HAMA; Human anti-mouse antibody response) initially received its clinical approval in 1997. In addition, complete human antibody, Humira received approval in 2003. Furthermore, in order to increase treatment efficacy, the research on bispecific antibodies, antibody drug conjugation (ADC), and long-lasting antibodies improving heavy-chain constant region (Fc) has been actively conducted.

In the case of antibodies for treating a solid tumor, during a process where the antibodies are transferred to tumor tissues, the amount of antibodies transferred to the tumor tissues in actual bodies of human beings is merely 0.01 to 0.001% of the amount injected by various barriers, which means that the treatment effect of antibodies is very limited (Thurber et al. 2008). Accordingly, the development of antibody technology allowing the antibodies to be selectively accumulated in the tumor tissues and to have high permeability into the tumor tissues may increase the treatment effect of antibodies and thus is very important.

There are two major reasons why the antibodies are not well permeated into tissues: 1) intrinsic properties of antibodies (size, antigen-binding properties, etc.) (Thurber and Dane Wittrup, 2012) and 2) fine physiological properties of tumor tissues which are different from normal tissues (Jain and Stylianopoulos, 2010).

Since antibodies are big molecules of 150 kDa consisting of 12 domains, the antibodies in the blood are difficult to be transferred to the tumor tissues through diffusion or convection (Baker et al. 2008). Thus, among the research conducted to solve this, there was an attempt to administer only the domain which binds to an antigen of antibody. In the case of single-chain antibody fragment (scFv, 30 kDa) and heavy-chain variable region (VHH, 14 kDa), they permeated into the tumor tissues much more than the antibodies themselves. However, as their size decrease, a great deal thereof come out through the kidney, and thereby a half-life gets shorter. Thus, efficacy of antibodies has not been significantly improved (Behr et al. 1998).

Another reason why the antibodies are not distributed in a large amount in the tissues is an antigen binding capacity of antibodies. The antibodies for treating the solid tumor are over-expressed in a tumor-associated antigen, or in a tumor, and have a high affinity to a target which is important for the tumor's growth. Even when the antibodies reach the tissues where a specific antigen is present, in the tumor tissues consisting of cells with a great amount of antigen expression, the antibodies are stayed in the antigen while binding to the antigen, due to their high affinity (Lee and Tannock, 2010). Also, after the binding, the antibodies penetrated into the cells along with antigens (Endocytosis) and are lysed. Consequently, the antibodies cannot exert their anti-cancer effects. In order to overcome this, the research for adjusting affinity or lengthening half-life has been processed (Dennis et al. 2007).

Physiological properties of tumor tissues which prevent the antibodies from being permeated and distributed in the tumor tissues may be broadly classified into 4 cases, which are endothelial barrier, high interstitial fluid pressure, stromal impediment, and epithelial barrier.

For the endothelial barrier, the tumor over-expresses and secretes factors (pro-angiogenic factor) which promote the growth of vascular endothelial cells located around blood vessel in order to receive a great deal of nutrients according to the tumor's rapid speed of growth. Accordingly, a large amount of new blood vessels are produced in an uneven manner, which leads to a decrease in the speed of entire blood flow. In order to overcome this, there is a method for increasing extravasation so that therapeutic agents could come out of the blood vessel and be distributed into the tissue. There is a case of enhancing a drug delivery into tumor tissue by co-administering TNF-α and IL02, which are cytokine inflammatory responses related with extravasation, chemical substance promoting extravasation (promoter chemical drug) (Marcucci et al. 2013), iRGD peptide, etc. in combination with therapeutic agents. However, these attempts were difficult to be commercialized and clinically experimented in that it is required to produce two substances of antibodies and extravasation promoter. Additionally, iRGD peptide reached its limit in that it needs to be administered in a great quantity (2 mg/kg or 4 mg/kg) (Sugahara et al. 2010).

High tumor interstitial fluid pressure results from a situation where the pressure difference allowing the drug to be convected from the blood vessel to the tissue is small, or where the fluid pressure of tissue is higher than that of blood. High tumor interstitial fluid pressure is mainly caused due to the accumulation of interstitial fluid pressure in the absence of lymphatic duct in the tumor tissue, unlike in the normal tissue, and contributes to abnormal angiogenesis. In order to overcome this, a method for preventing the operation of a factor promoting the growth of vascular endothelial cell, particularly vascular endothelial cell growth factor-A (VEGF-A), and inhibiting angiogenesis to normalize the blood vessel, or a method for increasing the fluid pressure of blood vessel has been attempted. With regard to the method for increasing the fluid pressure of blood vessel, there was a case where plasma protein albumin was administered in combination with antibodies to increase osmotic pressure of blood vessel, thereby improving delivery effect of antibodies to the tumor tissue (Hofmann et al. 2009).

The stromal impediment, which is an extracellular matrix barrier met when the antibodies come out to micro-vessels and are convected to the tissue, mainly consists of collagen and hyaluronan. The extracellular matrix greatly affects the shape of tumor. Accordingly, there is a big difference between the area where the drug is well distributed and the area where the drug is not well distributed, so drug distribution becomes uneven. Additionally, as an amount of expression of extracellular matrix increases, the tumor interstitial fluid pressure due to a high cell density with solid tumor stress (solid stress) increases. As the method for overcoming this, there is a method for inducing apoptosis of tumor tissue cell to reduce tumor interstitial cell density. Additionally, there was a case increasing the drug delivery effect about two times compared to a control group by processing an enzyme (collagenase) dissolving collagen in the tumor tissue to reduce solid stress (Eikenes et al. 2004).

In the epithelial barrier, intercellular adhesion factors of tumor interstitial epithelial cell densely fill up an intercellular space, and thus they prevent the therapeutic agent from being diffused and convected between the cells. E-cadherin is well known as a main factor of the intercellular adhesion. Since a substance reducing the E-cadherin was found in virus (adenovirus-3), there was a case where only a part (JO-1) with an activity of reducing E-cadherin of cell among proteins constituting the virus was administered in combination with the antibody, thereby increasing an anti-cancer effect of antibody (Beyer et al. 2011).

Considering the methods suggested so far to readily deliver the therapeutic agents to the tumor, most cases simply administer the therapeutic agents in combination with the substance for delivering this therapeutic agents well to the tumor tissue. Particularly, peptide is pharmacokinetics resulting from a small size of molecule, and has very short half-life. Thus, a great amount of peptide needs to be administered to actual patients and the administration needs to be frequently made. Furthermore, since the therapeutic agents and substances for tumor permeation operation need to be produced, respectively, which is an inevitable process during co-administration, its industrial practicability is low. Also, the peptide sequence and protein which do not exist in the natural world are likely to cause immunogenicity. Thus, ideally, it is required to develop a format where the antibody acquires tissue permeability as it is so that the delivery effect of one antibody molecule into the tumor tissue could be increased.

Among the proteins existing in the natural field, the vascular endothelial cell growth factor-A (VEGF-A) is well known for inducing blood spout (extravasation), which is also called as a vascular permeability factor. This action is known as a phenomenon caused by the binding with a vascular endothelial cell growth factor receptor (VEGFR2). Interestingly, in a mutant experiment of the vascular endothelial cell growth factor-A, even if the factor is not combined to the vascular endothelial cell growth factor receptor, vascular permeability increased, which suggests that another receptor of the vascular endothelial cell growth factor-A exists (Stacker et al. 1999). Other professionals of the same age found that this receptor is neuropilin (NRP).

Neuropilin was first found in a *Xenopus* nervous system. Neuropilin is a transmembrane glycoprotein, and has two types of NRP1 and NRP2. Neuropilin is expressed very weakly in normal cells, whereas is over-expressed in tumor vascular endothelial cells, solid tumor cells, blood tumor cells. Neuropilin operates as a coreceptor of VEGFRs (VEGF receptors) by binding to VEGF family ligands. Especially, NRP1 operates as a coreceptor of VEGFR1, VEGFR2 and VEGFR3, and binds to various VEGF ligands, thereby contributing to angiogenesis, cell survival, migration & adhesion, invasion, etc. in the tumor tissue. In comparison, NRP2 operates as a coreceptor of VEGFR2 and VEGFR3, thereby contributing to lymphangiogenesis and cell adhesion. Additionally, NRP1/NRP2 (NRP1/2) operates as a coreceptor of plexin family receptors to bind to secreted class 3 semaphorins (Sema3A, Sema3B, Sema3C, Sema3D, Sema3E, Sema3F and Sema3G). Since the neuropilin has no domain in functional cells, even if a ligand is binding thereto, the neuropilin has no activity by itself. It is known that signals are transferred through the VEGF receptor, which is the coreceptor, or through the plexin co-receptor. Sema3 binds to neuropilin and the plexin receptor at a ratio of 2:2:2 and operates.

There are cases reported that the operation of neuropilin and coreceptor is inhibited even when the neuropilin alone is targeted. For example, in the case of anti-neuropilin-1 antibody, it is reported that the anti-neuropilin-1 antibody is competitive to bind only to neuropilin-1 with VEGA-A, which is well known for binding to VEGFR2 and neuropilin-1, and has the function of inhibiting angiogenesis, cell survival, migration & adhesion and invasion, which are operations of VEGFR2 (Pan Q et al 2007). In the case of anti-neuropilin-2 antibody, it is reported that anti-neuropilin-2 antibody is competitive to bind to neuropilin-2 with VEGA-C which is well known for binding to VEGFR3 and neuropilin-2 at the same time, and has the function of inhibiting lymphangiogenesis and cell adhesion, which are operations of VEGFR3 (Cant M et al. 2008).

Thus, the present inventors infer a part of minimum Sema3A- or Sema3F-derived peptide with an enhancing effect of vascular endothelial cell permeability by the interaction between the neuropilin and Sema3A or Sema3F, and designed a mutant peptide so as to have a high affinity with the neuropilin. The present inventors designed bivalent shape by converging peptide into a heavy-chain C-terminus of antibody so that the peptide could copy the function of Sema3A/Sema3F operating as a homodimer. As this design is a single molecule fused with antibody-peptide, a unique function of antibody is maintained as it is. Additionally, by promoting the antibody's accumulation into the tumor tissue and permeability into the tumor tissue by the binding to the neuropilin, and additionally inhibiting the operation of neuropilin coreceptor by the neuropilin targeting, a fusion antibody technology with an anti-angiogenesis effect has been developed.

SUMMARY OF INVENTION

It is an aspect of the present invention to provide a tumor tissue-penetrating peptide (TPP) specifically binding to neuropilin.

It is another aspect of the present invention to provide a fusion protein, a small molecule drug, a nanoparticle, or a liposome having the tumor tissue-penetrating peptide fused therein.

It is another aspect of the present invention to provide a polynucleotide coding the tumor tissue-penetrating peptide, a recombinant vector including the same, a host cell transformed with this vector, and a method for preparing a tumor tissue-penetrating peptide using the host cell.

Also, it is another aspect of the present invention to provide a pharmaceutical composition for treating or preventing cancer or angiogenesis-related diseases, including the tumor tissue-penetrating peptide, or a fusion protein, a small molecule drug, a nanoparticle, or a liposome having the peptide fused therein.

Also, it is another aspect of the present invention to provide a composition for diagnosing cancer or angiogenesis-related diseases, including the tumor tissue-penetrating peptide, or a fusion protein, a small molecule drug, a nanoparticle, or a liposome having the peptide fused therein.

An aspect of the present invention provides a tumor tissue-penetrating peptide (TPP) specifically binding to neuropilin.

Another aspect of the present invention provides a fusion protein, a small molecule drug, a nanoparticle, or a liposome having the tumor tissue-penetrating peptide fused therein.

Another aspect of the present invention provides a polynucleotide coding the tumor tissue-penetrating peptide, a recombinant vector including the same, a host cell transformed with this vector, and a method for preparing a tumor tissue-penetrating peptide using the host cell.

Also, another aspect of the present invention provides a pharmaceutical composition for treating or preventing cancer or angiogenesis-related diseases, including the tumor tissue-penetrating peptide, or a fusion protein, a small molecule drug, a nanoparticle, or a liposome having the peptide fused therein.

Also, another aspect of the present invention provides a composition for diagnosing cancer or angiogenesis-related diseases, including the tumor tissue-penetrating peptide, or a fusion protein, a small molecule drug, a nanoparticle, or a liposome having the peptide fused therein.

The tumor tissue-penetrating peptide and a protein having the peptide fused therein of the present invention have the properties of specifically binding to neuropilin, and accordingly specifically accumulate in tumor tissues, widen intercellular gap between the tumor vascular endothelial cells to promote extravasation, and control intercellular gap between tumors within the tumor tissue to increase infiltration within tumor tissue to show a remarkably increased in vivo tumor-suppressing activity. Further, when a fusion antibody having Sema3A- and Sema3F-derived peptides and peptides with remarkably improved affinity of their wild-type peptides with neuropilin fused therein or in the antibody fragment are administered in the same dosage as a control group antibody having no peptide fused therein, they specifically accumulate in tumor tissues, and increase infiltration within tumor tissue, to show a remarkably increased in vivo tumor-suppressing activity, compared with the control group antibody.

An antibody having the tumor tissue-penetrating peptide of the present invention fused therein or a fragment thereof has the property of a bispecific antibody which has a binding capacity with neuropilin to which a tumor tissue-penetrating peptide binds, while maintaining the antigen binding capacity which the antibody originally has, and accordingly accumulates a fusion antibody with high efficiency in tumor tissues and increases infiltration within tumor tissues and thus is expected to have a high effect in treating and diagnosing tumor. Also, a fragment of the antibody having the tumor tissue-penetrating peptide of the present invention fused therein has the property of inhibiting angiogenesis by VEFG165A by inhibiting VEFG165A from binding to neuropilin 1/2, and thus is expected to be used for treating and diagnosing various diseases such as diabetic retinopathy, rheumatoid arthritis, or atherosclerosis, relating to angiogenesis.

An antibody having the peptide of the present invention fused therein or a fragment thereof shows a production yield similar to wild-type antibody which does not have a peptide fused therein, and thus there is no problem in mass production. Also, the fusion antibody or a fragment thereof maintains the antigen binding capacity which the wild-type antibody originally has, unique function of heavy-chain constant region (Fc), i.e., binding to FcRn (neonatal Fc receptor), and accordingly has a long serum half-life. Also, it has an advantage that the binding site (protein A and protein G) is preserved during the purification process, and the antibody-dependent cellular cytotoxicity and complement-dependent cellular cytotoxicity may be maintained.

BRIEF DESCRIPTION OF THE DRAWINGS

In FIGS. 1(A) and 1(B), semaphorin broadly includes three domains. From the N-terminus, a sema domain is a site binding to plexin, an Ig-like C2 type domain is a site binding to neuropilin a1 and a2, and a basic rich region is a site exposing a portion capable of binding to neuropilin by being cleaved by furin.

In FIG. 1(C), VEGF165A includes a site capable of binding to VEGFR2 (KRD) which is an original receptor of VEGF and a heparin-binding domain (HBD) capable of binding to neuropilin. Further, in each of semaphorin and VEGF165A, an interface forming a dimer is present.

In FIGS. 1(D) and (E), neuropilin broadly consists of five domains, and from the N-terminus, a1 and a2 domains are classified as CUB domains, and an Ig-like C2 type domain of semaphorin binds thereto. Particularly, this site forms a complex with plexin to increase binding capacity with semaphorin-plexin. The b1 and b2 domains are classified as FV/VIII domains, and the C-terminus of ligands of VEGF or class 3 semaphorins bind thereto. Particularly, in this portion, a site to which heparin is capable of binding is present and this facilitates the binding of ligands with many (+) charged residues. Further, MAM induces oligomerization, trans-membrane domain (TM) enables neuropilin to be fixed onto cell surface, and in a cytosolic domain, a site capable of binding to a Postsynaptic density 95, Disk large, Zona occludens 1 (PDZ) domain is present.

FIG. 4(A) illustrates a part encoding Fc-TPP of a cleavage map of a vector for expression in host cells. FIG. 4(B) illustrates a whole map of a vector for expressing Fc-TPP in host cells.

In FIG. 5(A), the antibody heavy-chain constant region was prepared starting from a hinge at N-terminus to maintain two disulfide bonds and facilitate formation of a dimer. The external exposure degree of TPP was regulated using the peptide linker of four amino acids GAGA (SEQ ID NO: 11) or fifteen amino acids GGGGS)3 (SEQ ID NO: 12) at the end of CH3, and thereafter 22 semaphorin derived sequences and improved derived sequences were added for preparation.

In FIG. 5(B), the formation of dimers of each clone on SDS-PAGE and purity upon purification can be confirmed. Also, the difference in size as much as the introduction of TPP can be confirmed.

FIG. 6(A) illustrates a comparison of the control group with Sema3A derived peptide and Fc-TPP, and FIG. 6(B) illustrates a comparison of the control group with Sema3F derived peptide and Fc-TPP. By comparison, stronger bond to neuropilin1/2 occurred in A22p and F22p peptides and Fc-A22p/F22p clones inducing mutants, and slightly stronger bond occurred in clones using (G4S)3 (SEQ ID NO: 12) linker among clones using GAGA (SEQ ID NO: 11) and (G4S)3 (SEQ ID NO: 12) linkers. No bond to the control group VEGFR2 was observed. Thereby, it was shown that TPP selectively binds to neuropilin.

FIG. 11b illustrates a result of Transwell assay performed for confirming whether TPP improves permeable capacity of HUVEC. As a result, VEGF165, Sema3A, Fc-15A22, Fc-15A22P, and Fc-15F22P effectively improved permeability. On the other hand, single forms of peptide, A22, A22P, F22, and F22P did not improve permeability. This result is closely related to the result of FIG. 11a.

FIG. 14(A) represents a part coding IgG heavy chain-TPP of map of a vector for expression in host cells. FIG. 14(B) represents a whole map of a vector for expressing IgG heavy chain-TPP in host cells.

FIG. 15(A) represents a part coding IgG light chain of map of a vector for expression in host cells. FIG. 15(B) represents a whole map of a vector for expressing IgG light chain in host cells.

FIG. 20a illustrates a result of IHC for confirming the infiltration capacity of Trastuzumab-TPP in tumor tissues. After injecting to nude mice each of human ovarian cancer cell line SK-OV-3 in which HER2 is expressed, Trastuzumab and Trastuzumab-15A22P were injected thereto to confirm infiltration capacity into tissue through double staining with blood vessels (CD31). As a result, it was confirmed that Trastuzumab infiltrated into the periphery of blood vessels, whereas Trastuzumab-15A22P infiltrates within the tissue to be further away from blood vessels (upper panel). This was quantified using Image J (lower panel).

FIG. 20b illustrates a result of Western blot performed from cancer cell tissues extracted from mice under the conditions of FIG. 19a.

BEST EMBODIMENT FOR CARRYING OUT THE INVENTION

Figure 1:
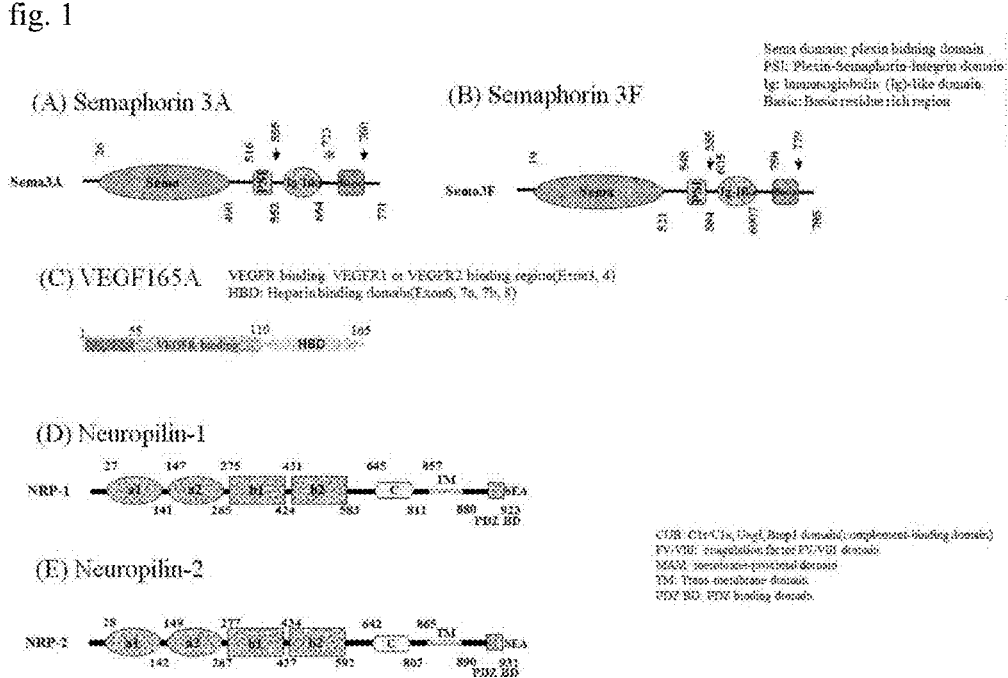
FIG. 1 is a schematic diagram illustrating the structures of semaphorins, VEGF165A, and neuropilin-1 and -2.

Hereinafter, the present invention will be described in more detail with examples. However, these examples are provided for illustrative purposes only, and are not intended to limit the scope of the present invention.

Example 1: Designs of Class 3 Semaphorin Ligands Derived Peptides Specifically Binding to Neuropilin and Peptides with Increased Affinity with Neuropilin In order to induce peptides specifically binding to neuropilin, sequences of ligands known to bind to neuropilin, i.e., vascular endothelial cell growth factor (VEGF-A, B, C, D), semaphorin 3-A, B, C, D, E, F (class 3 semaphorin), fibroblast growth factor-2 (FGF2), hepatocyte growth factor (HGF), and galectin-1 were analyzed.

Representatively, the whole sequences of VEGF-A and class 3 semaphorin were selected from the PubMed Entrez Protein Database.

As illustrated in FIGS. 1(A) and 1(B), secreted class 3 semaphorins (Sema3s) were identified from semaphorins 3A to 3G, and they have three domains in common. Upon investigation from the N-terminus, a sema domain is a site binding to plexin, an Ig-like C2 type domain is a site binding to neuropilin a1 and a2, and a basic rich region is a site exposing a portion capable of binding to neuropilin by being cleaved by furin.

As illustrated in FIG. 1(C), VEGF-A, which most strongly binds to neuropilin, among ligands of neuropilin known until now, particularly, VEGF165A, is divided into a site capable of binding to a primary receptor of VEGF, VEGFR2 and a heparin-binding domain (HBD) capable of binding to neuropilin. When binding to neuropilin-1, VEGF165A contains a portion (115-159, Exon7a, 7b) where there are many (+) charged residues binding to heparin which binds to neuropilin-1, in addition to the portion (160-165, Exon8a) binding to neuropilin-1. The portion where there are many (+) charged residues may cause a non-specific binding to heparin which resides in outer walls of cells. Also, VEGF165A contains cysteine at a portion corresponding to Exon8, and thus is expected to cause a decrease in an amount of expression, when VEGF165A is fused with a protein such as an antibody and expressed, and thus it is excluded.

As illustrated in FIGS. 1(D) and 1(E), neuropilin broadly consists of five domains, and from the N-terminus, a1 and a2 domains are classified as CUB domains, and an Ig-like C2 type of semaphorin binds thereto. Particularly, this site forms a complex with plexin, and plays a role of increasing the binding force with semaphorin-plexin. The b1 and b2 domains are classified as FV/VIII domains, and the C-terminus of VEGF family ligand or class 3 semaphorin ligand binds thereto. Particularly, in this portion, a site to which heparin is capable of binding is present and this facilitates the binding of ligands with many (+) charged residues.

Further, MAM induces oligomerization, trans-membrane domain (TM) enables neuropilin to be fixed onto cell surface, and in a cytosolic domain, a site capable of binding to a Postsynaptic density 95, Disk large, Zona occludens 1 (PDZ) domain is present.

Figure 2:
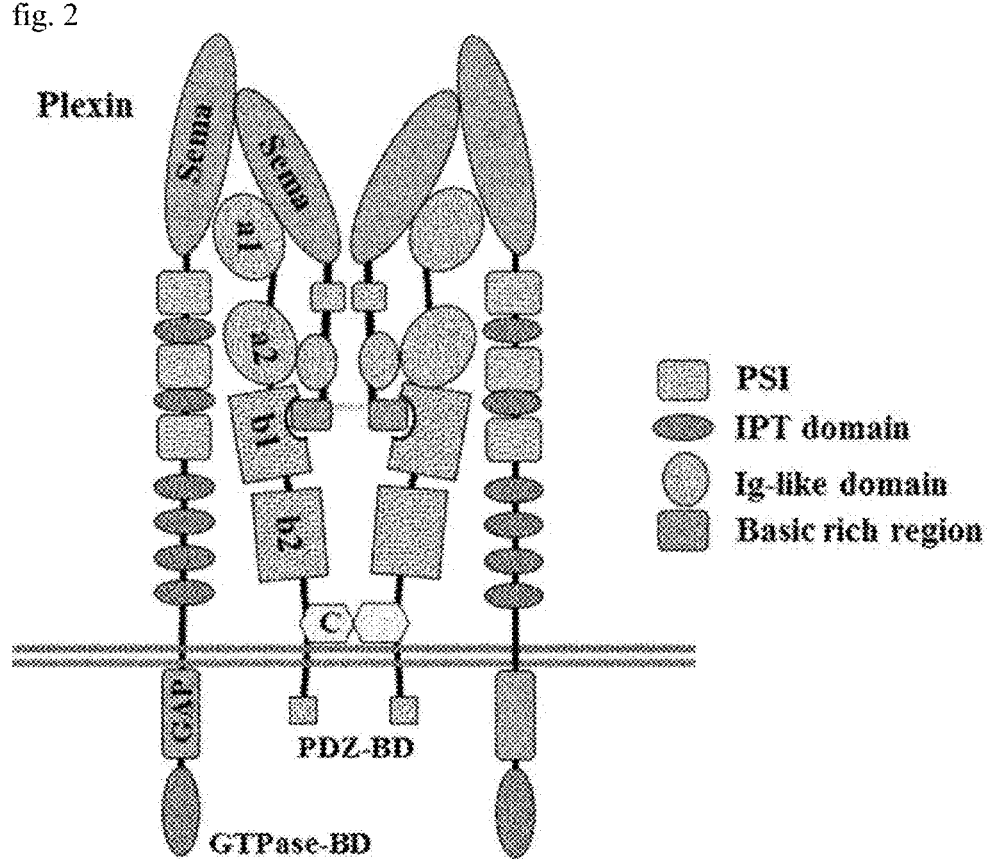
FIG. 2 is a schematic diagram illustrating a 2:2:2 complex including plexin of Sema3A and its co-receptor neuropilin. Sema3A and Sema3F present in nature form a homodimer, and the Sema domain interacts with the Sema domain of plexin. Further, the C-terminus of semaphorin interacts with b1 domain of neuropilin.

FIG. 2 is a schematic diagram illustrating a 2:2:2 complex including plexin of Sema3A and its co-receptor neuropilin. Sema3A and Sema3F present in nature form a homodimer, and the Sema domain interacts with the Sema domain of plexin. Further, the C-terminus of semaphorin interacts with b1 domain of neuropilin.

Figure 3:
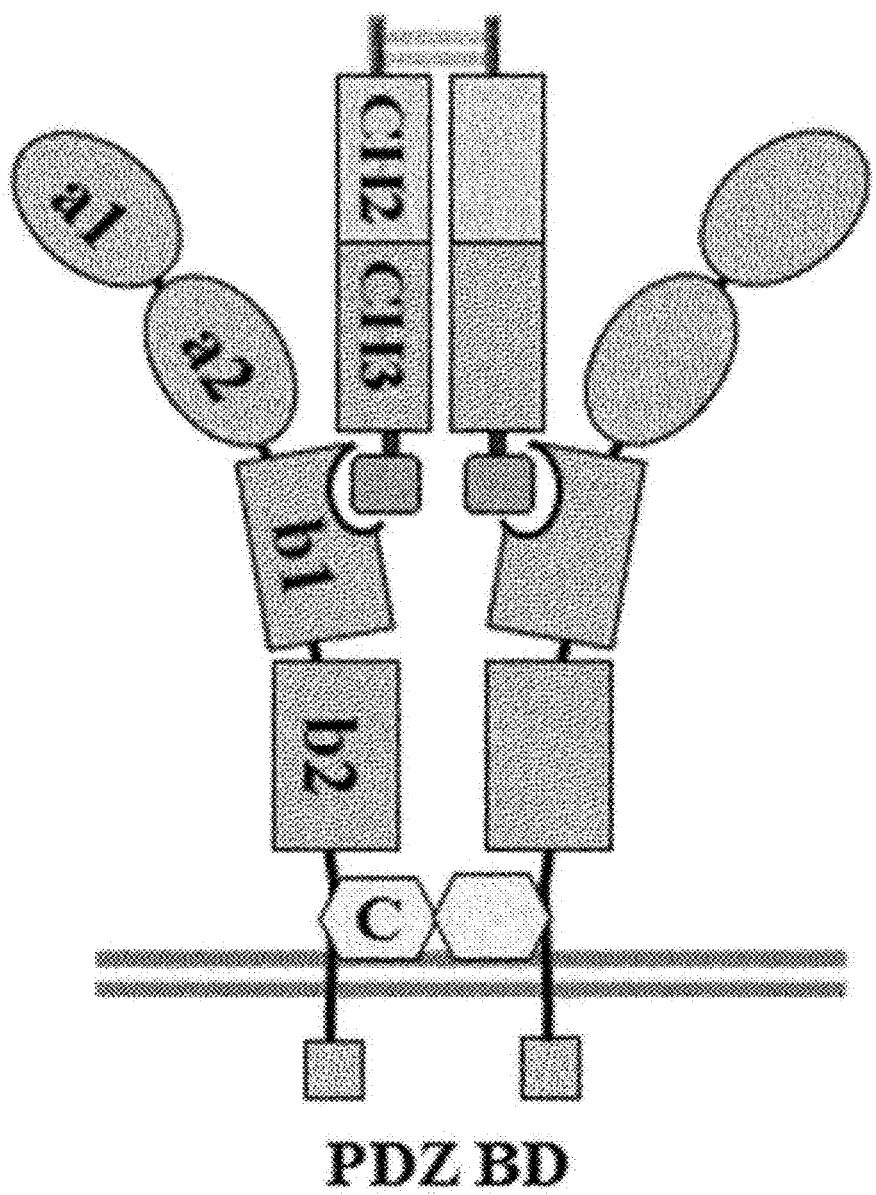
FIG. 3 is a schematic diagram illustrating a binding complex of neuropilin, ligand, and TPP fused antibody heavy-chain constant region (Fc-TPP). It was expected that each protein at its C-terminus binds to neuropilin (particularly, to b1 domain) in the form of dimer.

FIG. 3 is a schematic diagram illustrating a binding complex of neuropilin, ligand, and TPP fused antibody heavy-chain constant region (Fc-TPP). It was expected that similar to Sema3A and Sema3F present in nature, each protein at its C-terminus binds to neuropilin (particularly, to b1 domain) in the form of dimer.

As a result of sequence similarity analysis based on the structures and sequences of VEGF-A and class 3 semaphorin as above, it was found that there is a similarity in their C-terminus. Particularly, the binding of class 3 semaphorin to neuropilin is known to have activity after cleavage by furin, and here the similarity in the C-terminus of VEGF-A which interacts with neuropilin was found. This is shown in Table 1 below. The following Table 1 shows the result of amino acid sequence similarity analysis of C-terminal portions of class 3 semaphorins and VEGF-A family ligands which are ligands of neuropilin-1 and -2.

TABLE 1

| | |
|---|---|
| Sema3A (722-760) | CEQVWKRDRKQRRQRPGHTFGNSNKWKHLQENKKGR<u>N</u>RR |
| Sema3B (710-731) | CRP-----QPALQSL--PLE----------SRRKGR<u>N</u>RR |
| Sema3C (709-745) | CKDTRQQRQQGDESQ--KMRGDYGKLKALINSRKSR<u>N</u>RR |
| Sema3D (731-763) | CEQMWRREK--RRQR---NKGGP-KWKRMQEMKKKR<u>N</u>RR |
| Sema3E (734-770) | CTDRKRKKLKMSPSK--WKYANPQEKKLRSKPERYR<u>L</u>PR |
| Sema3F (756-779) | CQGYWRHVPPSPREA----PGAP-RSPEPQDQKKPR<u>N</u>RR |
| Sema3G (750-774) | CFRSRSRGKQARGKS----------WA---GLELGK<u>K</u>MK |
| VEGF165 (138-165) | CKNTDSRCKARQLEL-----------NERTCRCDK<u>P</u>RR |
| VEGF145 (110-145) | ARQEKKSVRGRGRGQ----RRRRKRSRYKSWSVCDK<u>P</u>RR |
| Clustal Consensus | .                                  : : |

(In Table 1, Sema3G(750-774) is identified by SEQ ID NO: 14, and the other sequences are C-terminal portions of those identified by the SEQ ID NOs in Table 2).

Based on the above sequence similarity, potential sequences are induced for introducing into an antibody from C-terminus to N-terminus of the portion where class 3 semaphorins are cleaved by furin. The following Table 2 shows the amino acid sequence information of potential binding sites of class 3 semaphorins and VEGF-A family ligands to neuropilin.

TABLE 2

| Nrp1/2 ligand | C-terminus sequence | |
|---|---|---|
| Sema3A | EQVWKRDRKQRRQRPGHTPGNSNKWKHLQENKKGRNRR | (SEQ ID NO: 15) |
| Sema3B | RPQPALQSLPLESRRKGRNRR | (SEQ ID NO: 16) |
| Sema3C | KDTRQQHQQGDESQKMRGDYGKLKALINSRKSRNRR | (SEQ ID NO: 17) |
| Sema3D | EQMWHREKRRQRNKGGPKWKHMQEMKKKRNRP | (SEQ ID NO: 18) |
| Sema3E | TDRKRKKLKMSPSKWKYANPQEKKLRSKPEHYRLPR | (SEQ ID NO: 19) |
| Sema3F | QGYWRHYVPPSPREAPGAPRSPEPQDQKKPRNRR | (SEQ ID NO: 20) |
| VEGF165 | ARQENPCGPCSERRKHLFVQDPQTCKCSCKNT DSRCKARQLELNERTCRCDKPRR | (SEQ ID NO: 21) |
| VEGF145 | ARQEKKSVRGKGKGQKRKRKKSRYKSWSVCDKPRR | (SEQ ID NO: 22) |
| VEGF121 | ARQEKCDKPRR | (SEQ ID NO: 23) |

22 amino acids were selected from the C-terminus sequence information of each of Sema3A and Sema3F of which binding capacity to neuropilin is well known. Specifically, A22 peptide having 22 amino acids derived from residues 739-760 which are part of the basic domain of Sema3A and F22 peptide having 22 amino acids derived from residues 758-779 which are part of the basic domain of Sema3F were selected.

Also, as a result of comparing amino acid sequences of potential neuropilin binding sites between class 3 semaphorins and VEGF-A family ligands, it was found that class 3 semaphorins preserved the third amino acid residue from C-terminus as asparagine (Asn), whereas VEGF-A family ligands which have high affinity with neuropilin preserved the residue as proline (Pro) (Table 2). Particularly, it was expected that the proline plays a role in limiting a domain to a specific structure in neuropilin interactions and greatly contributes to affinity between neuropilin-domains. In order to design a peptide with improved affinity with neuropilin using the same logic, A22p and F22p where the last third amino acids of A22 and F22 are replaced with proline were designed. The following Table 3 shows peptide sequences and SEQ ID NO. of A22 and F22 having amino acid sequences derived from C-terminus of Sema3A and Sema3F binding to neuropilin, and of A22p and F22p designed to increase affinity with neuropilin. The underlines are used to highlight the parts inducing mutants.

TABLE 3

| TPP Name | Ligand derived | Neuropilin target sequence | SEQ ID NO. |
|---|---|---|---|
| A22 | Sema3A | HTPGNSNKWKH LQENKKGR<u>N</u>RR | SEQ ID NO: 1 |
| A22p | Sema3A | HTPGNSNKWKH LQENKKGR<u>P</u>RR | SEQ ID NO: 2 |
| F22 | Sema3F | REAPGAPRSPE PQDQKKPR<u>N</u>RR | SEQ ID NO: 3 |
| F22p | Sema3F | REAPGAPRSPE PQDQKKPR<u>P</u>RR | SEQ ID NO: 4 |

Example 2: Construction of Fc-TPP where a Tumor Tissue-Penetrating Peptide (TPP) is Fused in an Antibody Heavy Constant Region Fc In order to perform experiments on the length of linkers for introducing four types of peptide sequences designed in the above Example 1 into C-terminus of a constant region Fc of a human antibody IgG1, linkers having 4 amino acids consisting of glycine, serine, and alanine, or 15 amino acids were selected. The selected linkers have sequences of GAGA (SEQ ID NO: 11) and (GGGGS)3 (SEQ ID NO: 12). The clone names and sequence information are shown in the following Table 4.

TABLE 4

| | Amino acid sequence fused to C-terminal of Fc (from N-terminus to C-terminus) | | Length of entire | |
|---|---|---|---|---|
| TPP Name | Linker sequence | Neuropilin target sequence | amino acid | SEQ ID NO. |
| 4A22 | GAGA | HTPGNSNEWKHLQEN KKGRNRR (SEQ ID NO: 1) | 26 | SEQ ID NO: 5 |
| 15A22 | GGGGSGGG GSGGGGS | HTPGNSNEWKHLQEN KKGRNRR (SEQ ID NO: 1) | 37 | SEQ ID NO: 6 |
| 15A22p | GGGGSGGG GSGGGGS | HTPGNSNKWKHLQEN KKGRPRR (SEQ ID NO: 2) | 37 | SEQ ID NO: 7 |
| 4F22 | GAGA | REAPGAPRSPEPQDQ KKPRNRR (SEQ ID NO: 3) | 26 | SEQ ID NO: 8 |
| 13F22 | GGGGSGGG GSGGGGS | REAPGAPRSPEPQDQ KKPRNRR (SEQ ID NO: 3) | 37 | SEQ ID NO: 9 |
| 15F22p | GGGGSGGG GSGGGGS | REAPGAPRSPEPQDQ KKPRPRR (SEQ ID NO: 4) | 37 | SEQ ID NO: 10 |

(in Table 4, GAGA is SEQ ID NO: 11; GGGGSGGGGSGGGGS is SEQ ID NO: 12.) Names and sequence information of TTPs and linkers linking to C-terminus of antibody heavy chain regions Peptides (SEQ ID NOS: 5-10) shown in Table 4 were fused to C-terminus of Fc, a constant region of human antibody IgG1, to have the properties of binding neuropilin in a bivalent form. This is designed to activate target neuropilin receptors, by copying Sema3A and Sema3F ligands which bind to neuropilin as homodimer.

Figure 4:
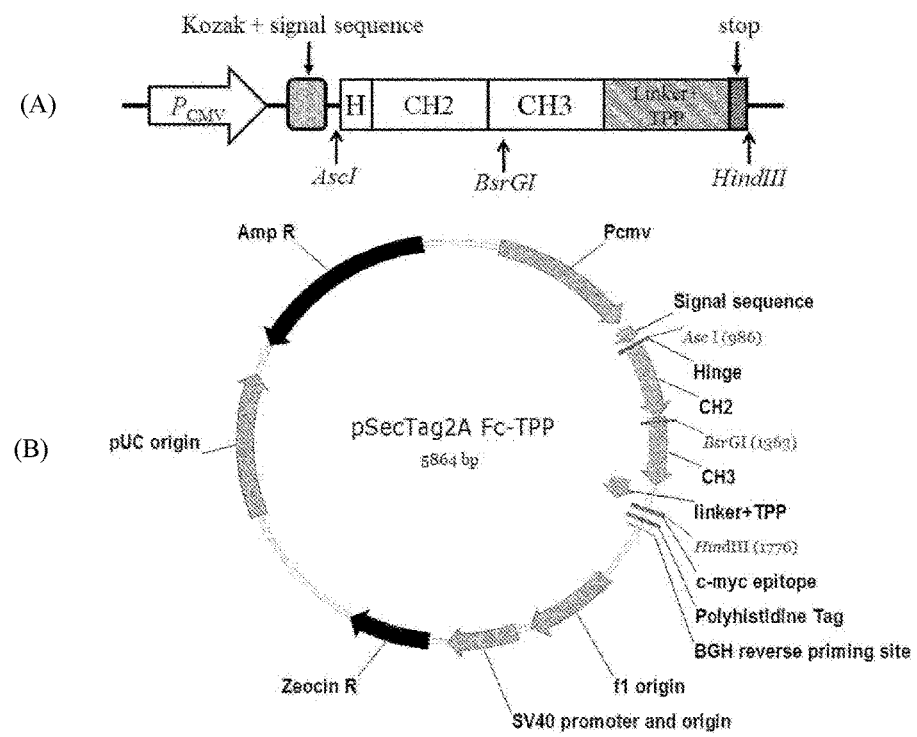
FIG. 4 is a schematic diagram illustrating a vector for expressing Fc-TPP in animal cells.

A Fc-TPP expression vector where the designed TPP is fused to C-terminus of Fc was cloned in an expression vector for animal cells to be implemented. FIG. 4(A) illustrates a part coding Fc-TPP of a cleavage map of a vector for expression in host cells. FIG. 4(B) illustrates a whole map of a vector for expressing Fc-TPP in host cells.

Before preparing Fc-TPP, Fc was cloned into the pSecTag2A vector with the restriction enzyme AscI/HindIII. Each Fc-TPP was substituted with the restriction enzyme BsrGI/HindIII from CH3 till the terminus by performing PCR with same forward primers starting from CH3 having Fc as a template and their respective reverse primers for introducing TPP into C-terminus.

Figure 5:
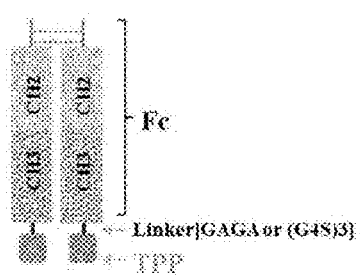
FIG. 5 is a schematic diagram illustrating TPP fused antibody heavy-chain constant region, and expression and purification SDS-PAGE.
Figure 5:
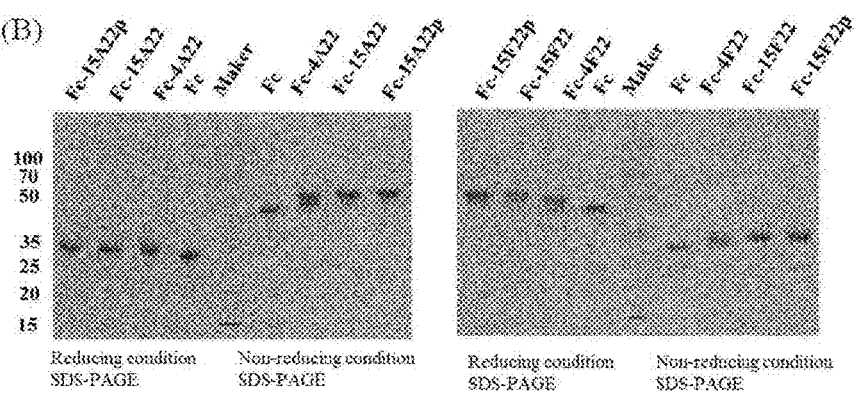

When Fc and Fc-TPP are expressed as above, they show different sizes as much as those of introducing TPP to purified proteins on SDS-PAGE (FIG. 5(B)) Fc was used as a control group for the size. Biotin-peptide of sequence derived from semaphorin consisting of 22 amino acids which was used as a control group was prepared by chemical synthesis (Peptron, Korea).

Example 3: Fc-TPP Expression and Purification

Proteins were expressed using transient transfection of plasmid (FIG. 4) encoding each Fc-TPP constructed in Example 2 above, with HEK293-F system (Invitrogen). In a shake flask, HEK293-F cells (Invitrogen) which were suspended and grown in the serum-free FreeStyle 293 expression medium (Invitrogen) were transfected with a mixture of plasmid and polyethylenimine (PEI) (Polyscience). When transfecting 200 mL in the shake flask (Corning), HEK293-F cells were seeded in 100 ml medium at a density of 2.0E*6 cells/ml and incubated at 120 rpm, 8% $CO_2$. Thereafter, plasmid encoding Fc-TPP was diluted in 10 ml FreeStyle 293 expression medium (Invitrogen) to be 250 μg (2.5 μg/ml), and mixed with 10 ml medium where PEI 750 μg (7.5 μg/ml) was diluted to be reacted at room temperature for 10 minutes. Then, the reacted mixture medium was put into the 100 ml seeded cells and incubated at 120 rpm, 8% $CO_2$ for 4 hours, and then the other 100 ml FreeStyle 293 expression medium was added thereto, followed by incubation for 7 days. The supernatant was collected after 7 days.

Proteins were purified from the collected cell culture supernatant by referring to the standard protocol. Antibodies applied to Protein A Sepharose column (GE healthcare) and were washed with PBS (pH 7.4). The antibodies were eluted at pH 3.0 using 0.1 M glycine buffer, and thereafter samples were immediately neutralized using 1 M Tris buffer. The buffer was changed to PBS (pH 7.4) using Pierce Dextran Desalting Column (5K MWCO). Thereafter, the eluted antibody fragments were concentrated using the centrifugal concentrator MILLIPORE Amicon Ultra (10 MWCO), and purified Fc-TPP was quantified using absorbance and absorption coefficient at wavelength 280 nm. The purified Fc-TPP was analyzed on SDS-PAGE under reducing and non-reducing conditions.

FIG. 5(A) is a schematic diagram illustrating TPP fused antibody heavy chain constant region. The antibody heavy-chain constant region was prepared starting from a hinge at the N-terminus to maintain two disulfide bonds and facilitate formation of a dimer. The external exposure degree of TPP was regulated using the peptide linker of GAGA (SEQ ID NO: 11) or (GGGGS)3 (SEQ ID NO: 12) at the end of CH3, and thereafter 22 semaphorin derived sequences were added for preparation.

FIG. 5(B) illustrates a result of analysis of SDS-PAGE of the purified Fc-TPP under reducing and non-reducing conditions. From FIG. 5(B), the formation and purity of dimmers of each clone on SDS-PAGE can be confirmed.

The following Table 5 shows the yields of proteins produced per 1 L medium of the purified TPP fused protein. The results obtained from three times experiments were statistics processed, and ± represents standard deviation. The obtained yields of proteins are not remarkably different from those of wild-type proteins.

TABLE 5

| Name of clone | Yield (mg/l) | Name of clone | Yield (mg/l) |
|---|---|---|---|
| Fc | 34.2 ± 4.8 | Fc-4F22 | 34.8 ± 2.1 |
| Fc-4A22 | 24.3 ± 4.7 | Fc-15F22 | 35.3 ± 9.8 |
| Fc-15A22 | 45.0 ± 8.3 | Fc-15F22p | 35.7 ± 5.8 |
| Fc-15A22p | 42.1 ± 8.6 | | |

Comparison of Fc-TPP Expression Purification Yields

Example 4: Confirmation on Binding Capacity of Fc-TPP to b1b2 Domains of Neuropilin-1 and -2

The binding capacity of purified Fc-TPP to b1b2 domains of neuropilin-1 and -2 (neuropilin (NRP)1/2-b1b1 domain) was confirmed in Enzyme Linked Immunosorbent Assay (ELISA).

As the control group, VEGF165A, Sema3A (26-760), Sema3F (19-779) and Fc, and their respective Fc-TPPs were biotinylated using the NHS-biotin kit (SIGMA-ALDRICH co., USA).

The target molecules, b1b2 domains (273-586) of neuropilin-1 and b1b2 domains (275-595) of neuropilin-2, and the control group VEGFR2 (46-753) were bound in an amount of 1 μg each in 96-well EIA/RIA plates (COSTAR Corning In., USA) at room temperature for 1 hour, and then washed three times for 10 minutes with 0.1% PBST (0.1% Tween20, pH 7.4, 137 mM NaCl, 10 mM Phosphate, 2.7 mM KCl, SIGMA-ALDRICH co., USA). After binding for 1 hour with 5% skim milk (pH 7.4, 137 mM NaCl, 10 mM Phosphate, 2.7 mM KCl, SIGMA-ALDRICH co., USA), it was washed three times for 10 minutes with 0.1% PBST (0.1% Tween20, pH 7.4, 137 mM NaCl, 10 mM Phosphate, 2.7 mM KCl, SIGMA-ALDRICH co., USA). For the control group, biotinylated VEGF165A, Sema3A, Sema3F and Fc, and for the experimental group, their respective Fc-TPPs and TPP peptides, were washed three times for 10 minutes with 100 nM (or were bound in a concentration of 1 μM of peptide and thereafter washed three times for 10 minutes with 0.1% PBST). After binding to alkaline phosphatase (AP)-conjugated anti-biotin mAb (Sigma, USA) and reacting with pnitrophenyl palmitate (pNPP, SIGMA-ALDRICH co., USA), absorbance at 405 nm was quantified. From the ELISA result obtained from 30 minute-reaction of AP-pNPP, the binding capacity of expressed and purified Fc-TPP to b1b2 domains of neuropilin-1 and -2 was confirmed.

Figure 6:
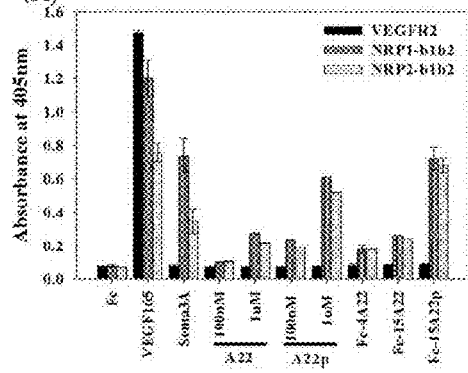
FIG. 6 illustrates a result of ELISA experiment for confirming the binding to b1b2 domains of NRP-1 and -2. VEGFR2-Fc, and b1b2 domains of NRP-1 and -2 were fixed onto plates, biotinylated peptides and Fc-TPP clones were bound at a concentration of 100 nM (in the case of peptides, 100 nM, 1 µM), and the binding was confirmed using anti-biotin antibody-alkaline phosphatase (AP) (SIGMA-ALDRICH co., USA) and pnitrophenyl palmitate (pNPP, SIGMA-ALDRICH co., USA).
Figure 6:
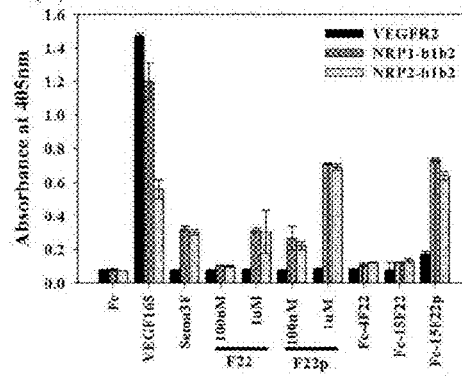

FIG. 6 illustrates a result of ELISA experiments for confirming the binding to b1b2 domains of neuropilin-1 and -2. FIG. 6(A) illustrates a comparison of the control group with Sema3A derived peptide and Fc-TPP, and FIG. 6(B) illustrates a comparison of the control group with Sema3F derived peptide and Fc-TPP. By comparison, stronger bond occurred in A22p and F22p peptides and Fc-A22p/F22p clones relatively inducing mutants, and slightly stronger bond occurred in clones using (G4S)3 (SEQ ID NO: 12) linker among clones using GAGA (SEQ ID NO: 11) and (G45)3 (SEQ ID NO: 12) linkers.

Example 5: Confirmation on Binding Specificity of Fc-TPP to b1b2 Domains of Neuropilin-1 and -2

In order to confirm the binding specificity of Fc-TPP to b1b2 domains of neuropilin-1 and -2, ELISA for binding competition of the control group VEGF165A and Sema3A was performed.

Specifically, b1b2 domains (273-586) of neuropilin-1 and b1b2 domains (275-595) of neuropilin-2 were bound in 96-well EIA/RIA plates (COSTAR Corning In., USA) at room temperature for 1 hour, and then washed three times for 10 minutes with 0.1% PBST (0.1% Tween20, pH 7.4, 137 mM NaCl, 10 mM Phosphate, 2.7 mM KCl, SIGMA-ALDRICH co., USA). After binding for 1 hour with 5% skim milk (pH 7.4, 137 mM NaCl, 10 mM Phosphate, 2.7 mM KCl, SIGMA-ALDRICH co., USA), it was washed three times for 10 minutes with 0.1% PBST (0.1% Tween20, pH 7.4, 137 mM NaCl, 10 mM Phosphate, 2.7 mM KCl, SIGMA-ALDRICH co., USA). Mixtures where Fc-15A22p (30 nM) and Fc-15F22p (30 nM) showing high binding force were mixed with VEGF165A (25 nM to 0.02 nM) and Sema3A (3.3 nM to 0.2 nM) per concentration were produced to bind to b1b2 domains of neuropilin-1 and -2. After binding to alkaline phosphatase (AP)-conjugated anti-biotin mAb (Sigma, USA) and reacting with pnitrophenyl palmitate (pNPP, SIGMA-ALDRICH co., USA), absorbance at 405 nm was quantified. From the ELISA result, it was confirmed that VEGF165A, Sema3A and Fc-TPP are competitive to bind to b1b2 domains of neuropilin-1 and -2.

Figure 7:
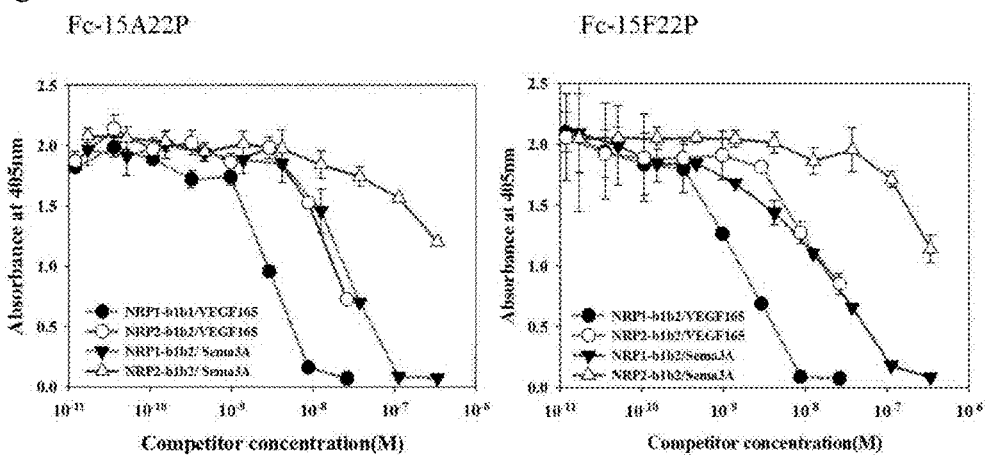
FIG. 7 confirms binding specificity of clones showing stronger binding capacity to neuropilin among Fc-TPP after confirming whether these clones are competitive with VEGF165A or Semaphorin3A to bind to neuropilin. It was confirmed that Fc-15A22p is competitive at a higher concentration of ligand than Fc-15F22p.

FIG. 7 illustrates a result of confirmation whether clones showing stronger binding force to neuropilin among Fc-TPP are competitive with VEGF165A and Sema3A to bind to neuropilin. As illustrated in FIG. 7, it was confirmed that Fc-15A22p is competitive at a higher concentration of ligand than Fc-15F22p.

Example 6: Confirmation on Binding Force of Fc-TPP to b1b2 Domains of Neuropilin-1 and -2

In order to more specifically confirm the binding force of Fc-TPP to b1b2 domains of neuropilin-1 and -2, surface plasmon resonance (SPR) was performed. Biacore2000 (GE healthcare) was used, and the binding force of VEGF165, Sema3F, Sema3A, Fc-4A22, Fc-4F22, Fc-15A22, Fc-15F22, Fc-15A22p and Fc-15F22p, of which binding capacity was confirmed by ELISA, to b1b2 domains of neuropilin-1 and -2 were analyzed.

Specifically, each b1b2 domain of neuropilin-1 and -2 was diluted with 10 mM Na-acetate buffer (pH 4.0), and fixed onto CM5 sensor chips (GE healthcare, USA) in about 1000 response units (RU). HBS-EP buffer (10 mM Hepes, 3 mM ethylenediaminetetraacetic acid, and 0.005% surfactant P20 (pH 7.4), GE Healthcare) was analyzed at a stream velocity 30 μl/min, and VEGF165 at a concentration of 80 nM to 5 nM, Sema3F and Sema3A at a concentration of 1 μM to 62.5 nM, and Fc-TPP at a concentration of 25 μM to 1.5625 μM were analyzed. After bond and dissociation analysis, the regeneration of CM5 chip was performed by streaming a buffer (20 Mm NaOH, 1 M NaCl, pH 10.0) at a stream velocity 30 μl/min for 1 minute. Each sensorgram obtained by 3 minute-bond and 3 minute-dissociation was normalized and subtracted by comparing with blank cells to calculate the binding affinity.

Table 6 shows a result of the binding affinity of Sema3A derived A22 peptide and a single mutant A22p in the form of Fc-TPP with b1b2 domains of neuropilin-1 and -2 (NRP 1 and 2), using surface plasmon resonance (SPR, BIACORE 2000, GE healthcare, USA). Table 7 shows a result of the binding affinity of Sema3F derived F22 peptide and a single mutant F22p in the form of Fc-TPP with b1b2 domains of neuropilin-1 and -2.

As shown in Tables 6 and 7, the difference in binding affinity between clones having GAGA (SEQ ID NO: 11) linker and clones having (GGGGS)3 (SEQ ID NO: 12) linker is about 10 times, when compared with Fc-4A22 and Fc-15A22. Pro mutant clones show the binding affinity about 100 times as high as those fused with wild-type peptide binding to neuropilin. At least 5 sensorgrams were used for analysis, and results obtained from twice experiments were statistics processed. ± represents standard deviation of results of individual experiments.

TABLE 6

| Clone | Receptors | Association rate ka (M$^{-1}$s$^{-1}$) | (Dissociation rate kd (s$^{-1}$) | Binding affinity K$_D$(M) |
|---|---|---|---|---|
| VEGF165 | NRP1-b1b2 | 9.75 ± 0.53 × 10$^5$ | 3.42 ± 0.29 × 10$^{-3}$ | 3.51 ± 0.36 × 10$^{-9}$ |
| VEGF165 | NRP2-b1b2 | 1.17 ± 0.12 × 10$^5$ | 3.73 ± 0.19 × 10$^{-3}$ | 3.20 ± 0.14 × 10$^{-8}$ |
| Sema3A | NRP1-b1b2 | 2.89 ± 0.07 × 10$^4$ | 8.08 ± 0.06 × 10$^{-4}$ | 2.79 ± 0.14 × 10$^{-8}$ |
| Sema3A | NRP2-b1b2 | 6.96 ± 0.03 × 10$^3$ | 1.61 ± 0.28 × 10$^{-3}$ | 2.31 ± 0.22 × 10$^{-7}$ |
| Fc-4A22 | NRP1-b1b2 | 1.02 ± 0.14 × 10$^3$ | 1.93 ± 0.05 × 10$^{-2}$ | 1.80 ± 0.14 × 10$^{-5}$ |
| Fc-4A22 | NRP2-b1b2 | 6.09 ± 0.63 × 10$^3$ | 1.23 ± 0.16 × 10$^{-1}$ | 2.02 ± 1.41 × 10$^{-5}$ |
| Fc-15A22 | NRP1-b1b2 | 4.86 ± 0.98 × 10$^3$ | 2.95 ± 0.04 × 10$^{-2}$ | 6.06 ± 0.42 × 10$^{-6}$ |
| Fc-15A22 | NRP2-b1b2 | 3.94 ± 0.42 × 10$^3$ | 3.87 ± 0.09 × 10$^{-2}$ | 9.8 ± 0.14 × 10$^{-6}$ |
| Fc-15A22p | NRP1-b1b2 | 9.15 ± 0.06 × 10$^3$ | 5.77 ± 0.16 × 10$^{-4}$ | 6.3 ± 0.21 × 10$^{-8}$ |
| Fc-15A22p | NRP2-b1b2 | 6.06 ± 0.04 × 10$^3$ | 3.76 ± 0.17 × 10$^{-4}$ | 6.2 ± 0.14 × 10$^{-8}$ |

TABLE 7

| Clone | Receptors | Association rate ka (M⁻¹s⁻¹) | Dissociation rate kd (s⁻¹) | Binding affinity $K_D$(M) |
|---|---|---|---|---|
| VEGF165 | NRP1-b1b2 | $9.75 \pm 0.53 \times 10^5$ | $3.42 \pm 0.29 \times 10^{-3}$ | $3.51 \pm 0.36 \times 10^{-9}$ |
|  | NRP2-b1b2 | $1.17 \pm 0.12 \times 10^5$ | $3.73 \pm 0.19 \times 10^{-3}$ | $3.20 \pm 0.14 \times 10^{-8}$ |
| Sema3F | NRP1-b1b2 | $3.98 \pm 0.69 \times 10^3$ | $9.73 \pm 0.19 \times 10^{-4}$ | $2.45 \pm 0.14 \times 10^{-7}$ |
|  | NRP2-b1b2 | $4.34 \pm 0.24 \times 10^3$ | $1.50 \pm 0.35 \times 10^{-3}$ | $3.45 \pm 0.32 \times 10^{-7}$ |
| Fc-4F22 | NRP1-b1b2 | $2.18 \pm 0.12 \times 10^2$ | $2.25 \pm 0.18 \times 10^{-3}$ | $1.03 \pm 0.04 \times 10^{-5}$ |
|  | NRP2-b1b2 | $1.21 \pm 0.15 \times 10^2$ | $1.57 \pm 0.40 \times 10^{-3}$ | $1.30 \pm 0.21 \times 10^{-5}$ |
| Fc-15F22 | NRP1-b1b2 | $1.35 \pm 0.24 \times 10^3$ | $5.34 \pm 0.24 \times 10^{-2}$ | $3.97 \pm 0.31 \times 10^{-5}$ |
|  | NRP2-b1b2 | $1.05 \pm 0.03 \times 10^3$ | $1.30 \pm 0.21 \times 10^{-2}$ | $1.24 \pm 0.18 \times 10^{-5}$ |
| Fc-15F22p | NRP1-b1b2 | $1.73 \pm 0.26 \times 10^4$ | $1.38 \pm 0.12 \times 10^{-3}$ | $7.97 \pm 0.51 \times 10^{-8}$ |
|  | NRP2-b1b2 | $1.34 \pm 0.24 \times 10^4$ | $1.23 \pm 0.16 \times 10^{-3}$ | $9.24 \pm 0.17 \times 10^{-8}$ |

Example 7: Confirmation on Specific Binding of Fc-TPP to Neuropilin-1 and -2 Expressed on Cell Surface First of all, in order to confirm the expression level of neuropilin-1 and -2 on the surface of cell lines used in the experiments for biological identification of TPP, FACS analysis was performed.

Figure 8:
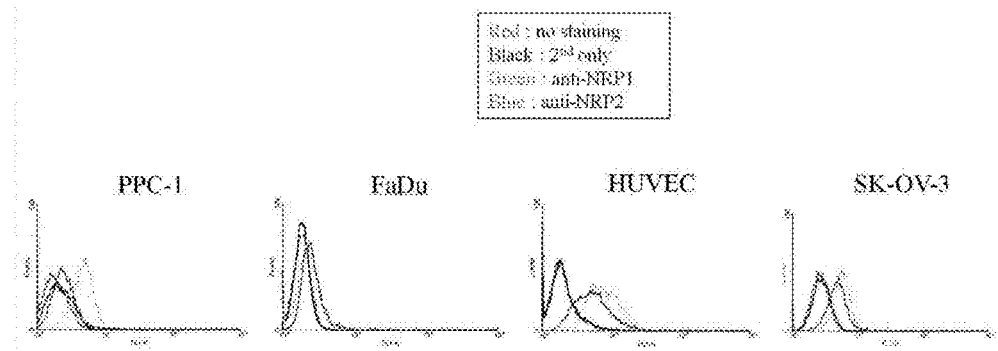
FIG. 8 illustrates a result of FACS analysis of expression level of neuropilin-1 and -2 on the surface of cell lines used for biological identification of TPP in this experiment. As a result of conducting experiments in human prostatic cancer cell line (PPC-1), human head and neck cancer cell line (FaDu), human endothelial cell line (HUVEC), and human ovarian cancer cell line (SK-OV-3), it was confirmed that neuropilin-1 and neuropilin-2 were expressed in each cell line.

FIG. 8 is a view illustrating that neuropilin-1 and -2 are expressed in cell lines. As illustrated, as a result of conducting experiments in human prostatic cancer cell line(PPC-1), human head and neck cancer cell line (FaDu), human endothelial cell line (HUVEC), and human ovarian cancer cell line (SK-OV-3), it was confirmed that neuropilin-1 and neuropilin-2 were expressed in each cell line.

In order to confirm whether Fc-TPP binds to neuropilin-1 and -2 expressed on cell surface, FACS analysis was performed, and Fc-15A22P and Fc-15F22P which were confirmed to specifically bind to neuropilin-1 and -2 were used.

Specifically, after incubating human ovarian cancer cell line (SK-OV-3) under conditions of 5% $CO_2$ and 37° C., $1 \times 10^5$ cells per sample were resuspended in a PBS buffer supplemented with 2% BSA and transferred to a FACS tube for conducting experiments. Each of Fc, Fc-15A22P, and Fc-15F22P were diluted with the buffer to be 1 μM and reacted at 4° C. for 1 hour, and then cellular binding proteins were stained using FITC-conjugated antibodies (Sigma) recognizing Fc for analysis with FACS Calibur (BD Bioscience).

Figure 9:
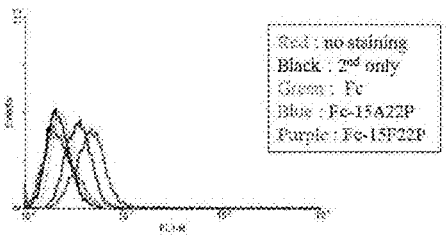
FIG. 9(A) illustrates a result of FACS analysis in human ovarian cancer cell line (SK-OV-3) in order to confirm whether Fc-TPP binds to neuropilin-1 and -2 expressed on the cell surface. In the above biochemical identification result (FIG. 6), Fc, Fc-15A22P, and Fc-15F22P having binding capacity to b1b2 domains of neuropilin-1 and -2 were treated under the same conditions to confirm their binding capacities. As a result, it was confirmed that unlike the control group Fc, Fc-15A22P and Fc-15F22P bind to cell surface.
FIG. 9(B) is a view illustrating a result confirming the binding capacity using the same manner as in the experiment of FIG. 9(A), after reacting purified b1b2 domains of neuropilin-1 and b1b2 domains of neuropilin-2 with each of Fc and Fc-TPP at room temperature in advance, in order to confirm that the binding capacity of Fc-TPP is specific to neuropilin-1 and -2 based on the result of FIG. 9(A). As a result, it was confirmed that the binding capacity of Fc-TPP was remarkably reduced in samples where b1b2 domains of neuropilin-1 and -2 in advance. This means that Fc-TPP binds specifically to neuropilin-1 and -2.
FIGS. 9(C) and 9(D) illustrates a result of FACS analysis for comparing binding sites among VEGF165A, Sema3A, and Sema3F, which have binding capacity to neuropilin-1 and -2. As a result, it was confirmed that the binding capacity of Fc-TPP was inhibited by VEGF165, the binding capacity of Fc-15A22P by Sema3A, and the binding capacity of Fc-15F22P by Sema3F.
Figure 9:
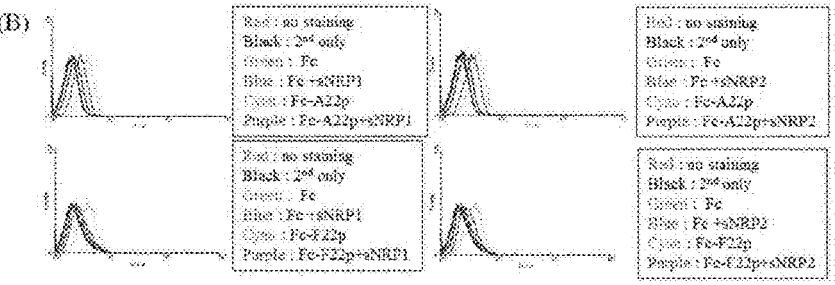
Figure 9:
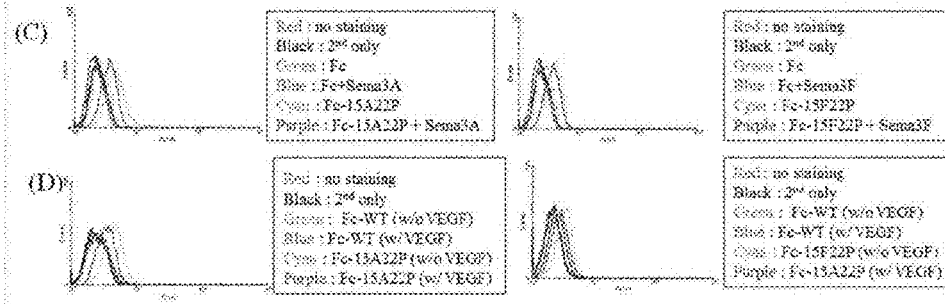
Figure 9:
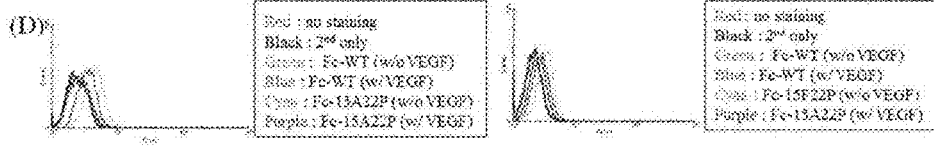

FIG. 9 illustrates a result of FACS analysis in human prostate cancer cell line (PPC-1) in order to confirm whether Fc-TPP binds to neuropilin-1 and -2 expressed on the cell surface. As illustrated in FIG. 9(A), it was confirmed that unlike Fc, Fc-15A22P and Fc-15F22P bind to the surface of PPC-1 cells.

Also, in order to confirm that such binding capacity is specific to neuropilin-1 and -2, 2 μM of b1b2 domains of neuropilin-1 and -2 which were used in the above experiments were mixed with each of 1 μM of Fc, Fc-15A22P, and Fc-15F22P and reacted at room temperature for 20 minutes. Then, the mixture was reacted with cell line SK-OV-3 at 4° C. for 1 hour in the same manner and proteins were stained for conducting FACS analysis. As illustrated in FIG. 9(B), it was confirmed that the binding capacity to Fc-TPP was remarkably reduced in samples where Fc-15A22P and Fc-15F22P were reacted in advance with b1b2 domains of neuropilin-1 and -2. This means that Fc-TPP binds specifically to neuropilin-1 and -2.

Additionally, in order to confirm the site where Fc-TPP binds to neuropilin-1 and -2, each of Fc-15A22P and Fc-15F22P was mixed with VEGF165A (1 μg/ml), and the binding capacity was confirmed in the same manner as above. As illustrated in FIG. 9(C), it was confirmed that the binding capacity was reduced by VEGF165A, and this means competitive binding with VEGF165A.

Also, Fc-15A22P and Fc-15F22P were mixed with Sema3A and Sema3F (100 μg/ml), respectively, which are ligands from which Fc-15A22P and Fc-15F22P were derived, and reacted, to confirm the binding capacity. As illustrated in FIG. 9(D), the binding capacity of each of Fc-15A22P and Fc-15F22P was reduced by Sema3A and Sema3F. This means that the binding of Fc-TPP to neuropilin-1 and -2 is specific similar to the original ligands.

Example 8: Specific Penetrating Capacity of Fc-TPP into Cells Through Neuropilin-1 and -2

In order to confirm whether Fc-TPP has intracellular penetrating capacity by neuropilin-1 and -2, like other neuropilin ligands having intracellular penetrating capacity, confocal microscopy was used to observe intracellular penetration and co-localization with neuropilin-1 and -2.

Specifically, $5 \times 10^4$ PPC-1 cells were plated into 24-well plates containing DMEM medium 0.5 ml supplemented with 10% FBS per well, followed by incubation at 37° C. for 24 hours at 5% $CO_2$. When the cells were stabilized, each well was washed with PBS 0.5 ml. Then, Fc, Fc-15A22P, and Fc-15F22P were diluted with 0.5 ml of transfection optimized medium (TOM, WelGENE Inc., Korea) to be 1 μM, followed by incubation at 37° C. for 1 hour under 5% $CO_2$ condition. After the medium was removed and each well was washed with PBS, Fc-TPP was stained with an antibody (Sigma) which specifically recognizes the FITC (green fluorescence)-conjugated Fc, and neuropilin-1 and -2 was stained with a primary antibody (SantaCruz) which recognizes each of them and with a TRITC (red fluorescence)-conjugated secondary antibody (Sigma). Nuclei were stained (blue fluorescence) with DAPI and observed under confocal microscopy.

Figure 10:
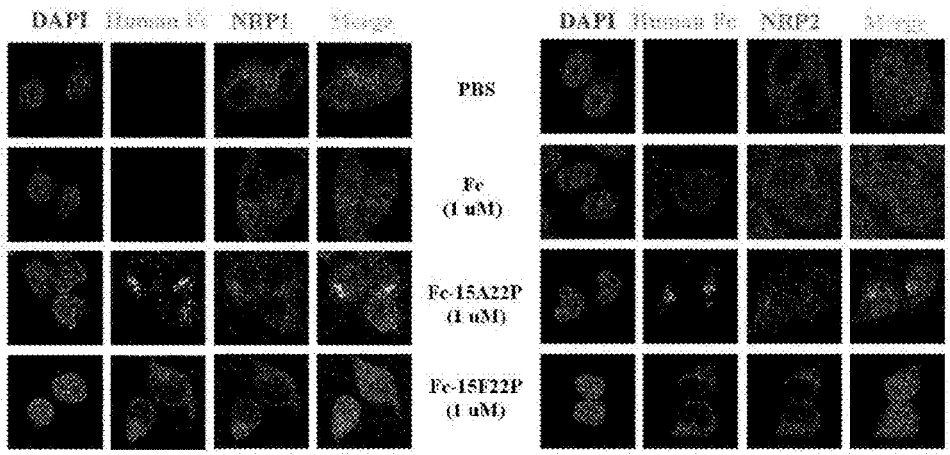
FIG. 10 illustrates a result of observation of co-localization of Fc-TPP and neuropilin-1 and -2 through confocal microscopy analysis, in order to confirm the specific intracellular penetrating capacity of Fc-TPP into neuropilin. After treating human prostate cancer cell line PPC-1 with PBS, Fc, Fc-15A22P, and Fc-15F22P under the same conditions and staining the degree of infiltration into cells, it was observed that unlike Fc, Fc-15A22P and Fc-15F22P penetrated into cells. Further, it was confirmed that Fc-TPP and neuropilin-1 and -2 co-localize and thereby the penetrating capacity of Fc-TPP is specific to neuropilin-1 and -2.

FIG. 10 illustrates a result of observation of co-localization of Fc-TPP and neuropilin-1 and -2 through confocal microscopy analysis, in order to confirm the specific intracellular penetrating capacity of Fc-TPP through neuropilin. As illustrated in FIG. 10, it was confirmed that the control group Fc did not penetrate into cells, whereas Fc-15A22P and Fc-15F22P penetrated into cells and were co-localized with neuropilin-1 and -2, respectively. This means that Fc-TPP has specific penetrating capacity by neuropilin-1 and -2.

Example 9: Confirmation on Cell Permeability Improvement of Fc-TPP (1) Western Blot for Examining Biological Mechanism of Fc-TPP in HUVEC Sema3A or VEGF165A is known to increase vascular permeability using neuropilin-1 (NRP1) as a co-receptor.

During this process, a decrease in vascular endothelial (VE)-cadherin, phosphorylation, etc. of endothelial cells occur. That is, VE-cadherin or epithelial (E)-cadherin involves in adhesion between endothelial cells, while forming the base of adherent junction between endothelial cells and epithelial cells. The change in molecules relieve the density of adherent junction, which results in increasing permeability of blood vessels and improving intracellular permeability.

As an experimental method for indirectly confirming improvement of vascular permeability based thereon, a change in VE-cadherin was confirmed through a Western blot. Specifically, HUVECs were seeded into 6-well plates at a density of $3 \times 10^5$ per well, followed by incubation for 24 hours. Thereafter, single peptides and Fc-TPP were treated with 1 μM for 10 minutes to perform a Western blot. Gel subjected to SDS-PAGE was transported into PVDF membrane, a primary antibody (SantaCruz) and an HRP-conjugated secondary antibody (SantaCruz) which recognize VE-cadherin and (3-actin, respectively were used for detection. ImageQuant LAS4000 mini (GE Healthcare) was used for analysis.

Figure 11A:
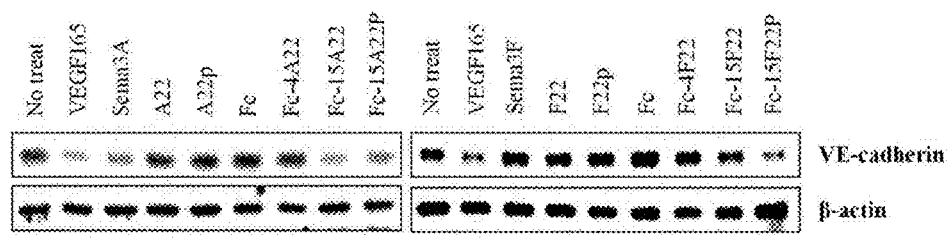
FIG. 11a illustrates a result of Western blot for identifying biological mechanism of Fc-TPP in HUVEC. Further, in order to confirm an effective format for TPP, single forms of peptide, A22, A22P, F22, and F22P were used, and for comparison depending on linker length with TPP, fusion types of Fc format, Fc-4A22, Fc-15A22, Fc-15A22P, Fc-4F22, Fc-15F22, and Fc-15F22P were used. The control group VEGF165A and Sema3A, unlike Sema3F, showed improvement of permeability in HUVEC, and this can be indirectly confirmed by a decrease in VE-cadherin. In the case of Sema3A derived TPP, Fc-15A22 and Fc-15A22P effectively decreased VE-cadherin, and VEGF165A and Sema3A showed the same result. Further, in the case of Sema3F derived TPP, the original ligand Sema3F did not induce a change in VE-cadherin, but Fc-15F22P decreased VE-cadherin under the same conditions.

FIG. 11a illustrates a result of Western blot for identifying biological mechanism of Fc-TPP in HUVEC. As illustrated in FIG. 11a, in the case of Sema3A derived protein, when treating the control group VEGF165A and Sema3A, a decrease in VE-cadherin was observed. In the case of single peptides A22 and A22P, no change in VE-cadherin was observed. Also, in the case of Fc and Fc-4A22, VE-cadherin was not decreased, whereas in the case of Fc-15A22 and Fc-15A22P, VE-cadherin was decreased (left panel). In the case of Sema3F derived TPP, only the control group VEGF165A and Fc-15F22P induced a decrease in VE-cadherin (right panel).

(2) Transwell Assay for Confirming Vascular Endothelial Cell Permeability of Fc-TPP Based on the above experimental results, as experiments for confirming the improvement of vascular endothelial cell permeability, single peptides and Fc-TPP were treated to conduct Transwell assay.

Specifically, HUVECs were seeded into Transwell plate (Corning) at a density of $5 \times 10^4$ per well in a upper chamber using Endothelial Growth Medium, PromoCell (EGM) medium, followed by incubation at 37° C. for 3 days under 5% $CO_2$ condition. Thereafter, after changing the medium to Endothelial Basal Medium (EBM, PromoCell), the control group VEGF165A, Sema3A and Sema3F were treated with about 1.3 nM and single peptides and Fc-TPP with 1 μM for 30 minutes. Thereafter, Dextran-FITC (Sigma) 50 μg was put into the upper chamber and the medium of the lower chamber was sampled to measure its fluorescence after 30 minutes, using the principle that a fluorescent substance is observed in the lower chamber when the permeability in HUVECs was improved.

Figure 11B:
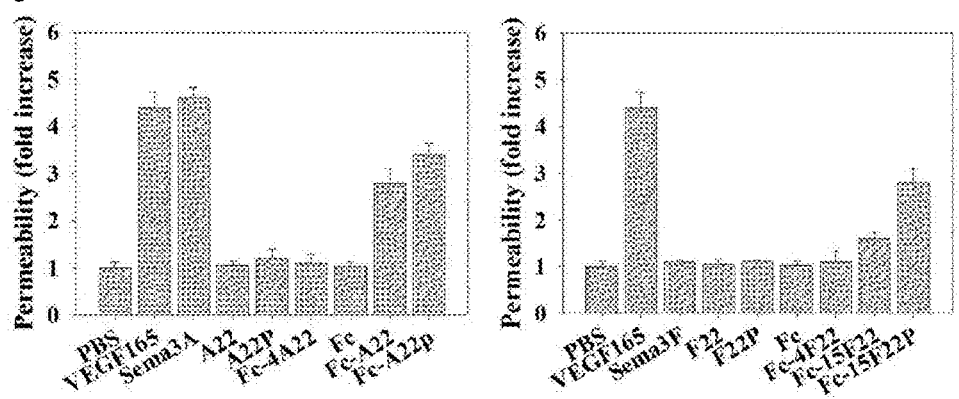

FIG. 11b illustrates a result of Transwell assay performed for confirming whether TPP improves permeability of HUVEC. As illustrated in FIG. 11b, it was confirmed that in the case of VEGF165A and Sema 3A, permeability of HUVEC was improved, and in the case of single peptides A22 and A22P, and Fc-4A22 with short Fc part and linker of TPP, the improvement of vascular permeability was not induced. On the other hand, in the case of fusion forms Fc-15A22 and Fc-15A22P, it was confirmed that permeability of HUVEC was improved. In the case of Sema3F derived TPP, HUVEC permeability was not improved by Sema3F itself, but in the case of Fc-15F22P, the improvement of vascular permeability was induced. Also, in the case of single peptides F22 and F22P, and in the case of fusion forms with lower binding capacity, Fc-4F22 and Fc-15F22, permeability of HUVEC was not improved.

(3) Immunohistochemistry (IHC) Experiment for Confirming Permeability of Fc-TPP in Mouse Models From Examples 9(1) and 9(2) above, it was confirmed that Fc-TPP improves permeability of Fc-TPP to vascular endothelial cells in vitro. Accordingly, in order to confirm the improvement of Fc-TPP's permeability in mouse models, immunohistochemistry (IHC) experiment was conducted.

As an experiment for confirming the improvement of Fc-TPP's permeability in tumor tissues, A431 cells were injected into Balb/c nude mice with subcutaneous injection at a density of $5 \times 10^6$ per mouse, and when the tumor volume became about 300 to 400 $mm^3$ after about 9 days, each of PBS, Fc, Fc-15A22P and peptide A22P in an amount of 5 mg/kg was intravenously injected. 3 hours after injection, tumors were extracted from mice to conduct immunohistochemistry experiment. The extracted tumors were cut into 20 μm thick using a frozen section method, and stained with a primary antibody, CD31 antibody (BD Pharmingen), and a TRITC (red fluorescence)-conjugated secondary antibody. Further, in order to observe Fc-TPP distributed in the tissues, FITC (green fluorescence)-conjugated antibodies recognizing Fc were used.

Figure 11C:
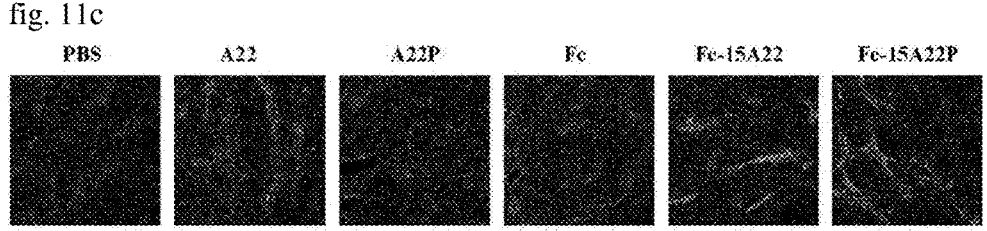
FIG. 11c illustrates a result of immunohistochemistry for confirming TPP's infiltration capacity in actual tumor tissues. Human epidermoid carcinoma cell line A431 was transplanted into nude mice to confirm the effect of TPP through double staining with blood vessels (CD31). As a result, it was confirmed that unlike peptide A22P and the control group Fc, Fc-15A22 and Fc-15A22P selectively reached tumor cells, and effectively infiltrated into tumor cells.

FIG. 11c illustrates a result of immunohistochemistry for confirming TPP's infiltration capacity in actual tumor tissues. As illustrated in FIG. 11c, single peptides A22 and A22P did not infiltrate into the tissues, whereas, unlike the control group Fc, the fusion forms Fc-15A22 and Fc-15A22P selectively reached tumor tissues, and they infiltrated into tumor cells. Also, it was confirmed that Fc-15A22P having higher binding capacity to neuropilin-1 and -2 than Fc-15A22 infiltrated into tissues more effectively.

(4) In Vivo Evans Blue Assay for Confirming Vascular Permeability

Figure 11D:
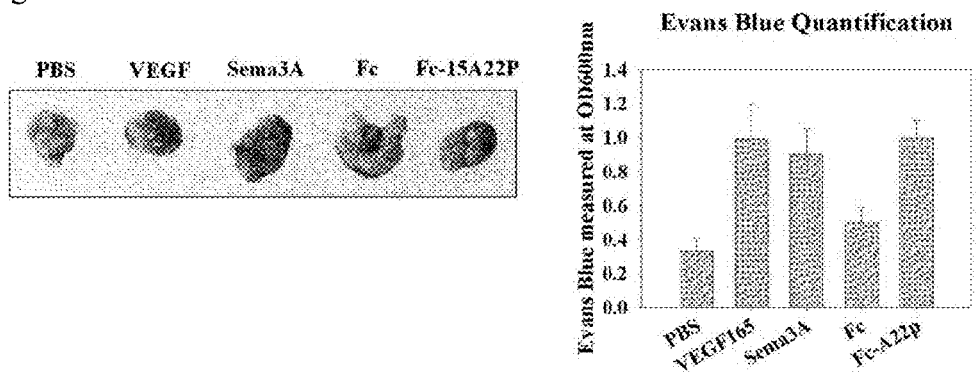
FIG. 11d illustrates a result of confirming the improvement of vascular permeability through Evans Blue assay. As a result, it was confirmed that unlike Fc, Fc-15A22P effectively improved tissue infiltration capacity, as shown in the above result.

Additionally, in order to confirm the improvement of vascular permeability in vivo, Evans Blue assay was conducted. As an experiment, FaDu cells were injected into Balb/c nude mice (Nara Bio, 4-week-old, female) with subcutaneous injection at a density of $5 \times 10^6$ per mouse, and when the tumor volume became about 500 $mm^3$ after about 10 days, Evans Blue (Sigma) 1 mg, and each of PBS, Fc, and Fc-15A22P in an amount of 7.5 mg/kg was intravenously injected. As a control group, VEGF165A (400 ng) and Semaphorin 3A (400 ng) were injected under same conditions. 40 minutes after injection, the mice were perfused through the heart with PBS containing 1% BSA, and tumor tissues were extracted (FIG. 11d). Then, the extracted tissues were put into 1 ml of 2,2N-methylaformamide (Sigma) and reacted at 37° C. overnight under mild shaking condition. Thereafter, the supernatant was obtained from centrifugation to measure the absorbance (600 nm), and the amount that Evans Blue penetrated was quantified.

FIG. 11d illustrates a result of confirming the improvement of vascular permeability through Evans Blue assay. The left panel is a photograph of cancer cells extracted, and the right panel illustrates a result of measuring absorbance (600 nm) for quantifying the Evans Blue. As illustrated in FIG. 11d, it was confirmed that VEGF165A and Sema3A increased vascular permeability as already known, and that Fc-15A22P also increased vascular permeability, unlike Fc.

(5) Confirmation on Effect of TPP on Cancer Cells

In order to confirm the effect of TPP on cancer cells, a change in E-cadherin was analyzed in human head and neck cancer cell line FaDu, under the same conditions as above experiments through Western blot.

Figure 11E:
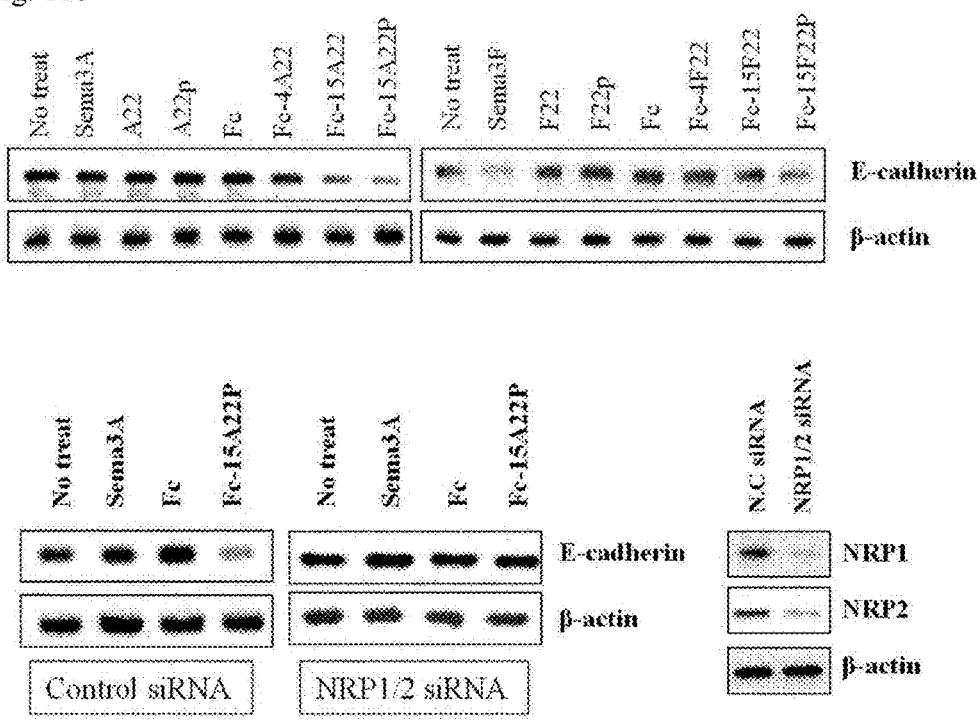
FIG. 11e illustrates a result of Western blot for a change in E-cadherin in human head and neck cancer cell line FaDu, in order to confirm the effect in cancer cell as well as vascular endothelial cell. As a result, in the case of Sema3A derived TPP, Fc-15A22 and Fc-15A22P induced a decrease in E-cadherin, unlike Sema3A, and in the case of Sema3F derived TPP, Fc-15F22P, like Sema3F, induced a decrease in E-cadherin. Further, upon reducing the expression of neuropilin-1 and -2 by co-injection of neuropilin-1 and -2 with siRNA, it was confirmed that Fc-TPP did not cause a decrease in E-cadherin, and thereby it was confirmed that Fc-TPP induced a decrease in E-cadherin specifically to neuropilin.

FIG. 11e illustrates a result of Western blot for a change in E-cadherin in human head and neck cancer cell line FaDu. As illustrated in FIG. 11e, Sema3A derived TPP did not induce a change in E-cadherin, whereas Fc-15A22 and Fc-15A22P induced a decrease in E-cadherin. Also, Sema3F induced a decrease in E-cadherin and when treated with Fc-15F22P, E-cadherin was decreased.

Upon collectively analyzing the above experimental results, Fc-TPP was constructed from peptides derived from each of Sema3A and Sema3F, but the original proteins and peptides derived therefrom did not always induce the same results in the properties of original proteins, specificity to neuropilin-1 or neuropilin-2, and tendency of signal transduction such as a decrease in VE-cadherin or E-cadherin. Further, peptides having binding capacity to neuropilin-1 and -2 did not induce signal transduction by TPP as single forms, whereas the fusion form Fc-TPP effectively induced signal transduction. This means that signal transduction by neuropilin-1 and -2 is effective in the fusion form of Fc-TPP. Also, Fc-4A/F22 did not induce signal transduction, whereas Fc-15A/F22 and Fc-15A/F22P induced signal transduction. This means that the fusion form Fc-TPP more effectively induces signal transduction by neuropilin-1 and -2, than signal form peptides, and that the effect varies depending on the length of linkers of Fc-TPP.

Example 10: Confirmation on Capacity of Fc-TPP to Inhibit Angiogenesis (1) Tube Formation Assay for Confirming Capacity of Fc-15A22P to Inhibit Tube Formation in HUVEC VEGF165A is known to form new blood vessels (angiogenesis) using neuropilin-1 as a co-receptor. As an experiment confirming angiogenesis in vitro based thereon, tube formation assay was conducted. As an experimental method, 50 µl of ECMatrix was injected into 96-well plates and polymerized at 37° C. for 2 hours. After 2 hours, HUVEC cells were suspended using Endothelial basal medium (EBM, PromoCell) and plated on ECMatrix at a density of $1\times10^4$ per well by mixing with VEGF165A (20 ng/ml), Fc, Fc-15A22P (1 µM), followed by incubation for 8 hours. The incubated cells were observed by a microscope to obtain images.

Figure 12A:
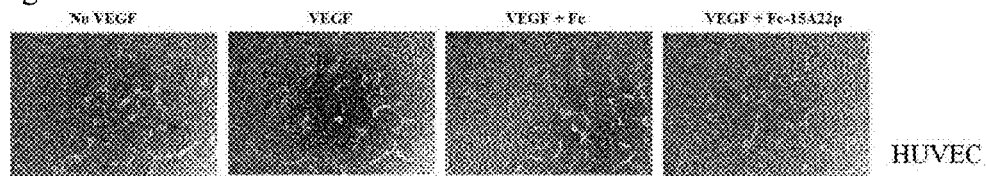
FIG. 12a illustrates a result of tube formation assay performed for confirming whether Fc-15A22P inhibits tube formation of vascular endothelial cell by VEGF165A. As a result, it was confirmed that Fc-15A22P effectively inhibited the tube formation of endothelial cell induced by VEGF165A.

FIG. 12a illustrates a result confirming the capacity to inhibit tube formation through tube formation assay. As illustrated in FIG. 12a, it was confirmed that VEGF165A increased tube formation as already known, and that Fc-15A22P, unlike Fc, inhibited the tube formation.

Figure 12B:
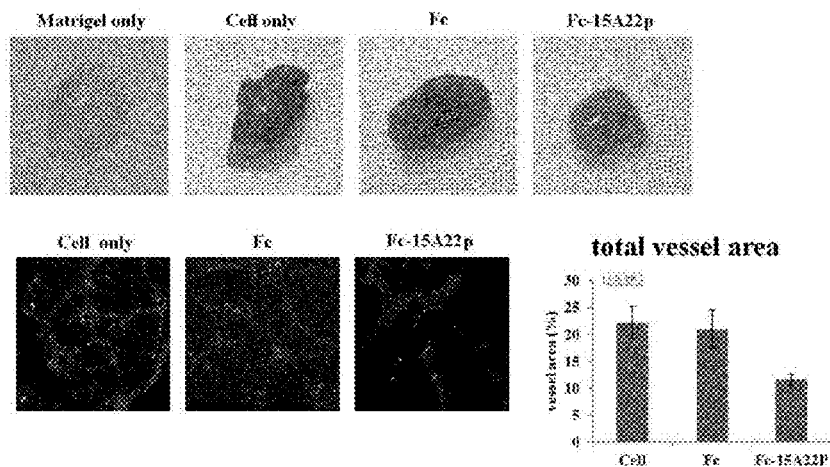
FIG. 12b performed in vivo matrigel plug assay on mice, in order to identify whether Fc-15A22P can inhibit angiogenesis induced by VEGF165A. Also, the density of blood vessels was measured with anti-CD31 antibody through immunohistochemistry. As a result, it was confirmed that Fc-15A22P can inhibit angiogenesis induced by VEGF165A.

(2) In Vivo Matrigel Plug Assay for Confirming Capacity of Fc-15A22P to Inhibit Angiogenesis Additionally, in order to confirm capacity to inhibit angiogenesis in vivo, matrigel plug assay was conducted. As an experimental method, $7.5\times10^6$ A431 cells per mouse, 80 µg of Fc or Fc-15A22P, and 0.4 ml of Matrigel (BD Biosciences) were subcutaneously injected into 6 to 8-week old balb/c nude mice. 9 days after injection, matrigel plug was removed to take photographs of the image (FIG. 12b), and cut into 20 µm thick using a frozen section method to perform immunohistochemistry experiments. Blood vessels were stained with a primary antibody, CD31 antibody, and a TRITC (red fluorescence)-conjugated secondary antibody recognizing the primary antibody, to measure the density of the blood vessels. FIG. 12b illustrates a result confirming that Fc-15A22P is capable of inhibiting angiogenesis induced by VEGF165A in mice in vivo.

Example 11: Confirmation on mAb-TPP Production and Antigen Binding Capacity (1) Vector for mAb-TPP Production, and Expression and Purification Thereof Example 9 above confirmed that Fc-TPP improves the permeability of vascular endothelial cells in vitro and in vivo. Accordingly, TPP was fused to Fc terminus of antibodies as a format for verifying the effect of TPP in mouse models.

Figure 13:
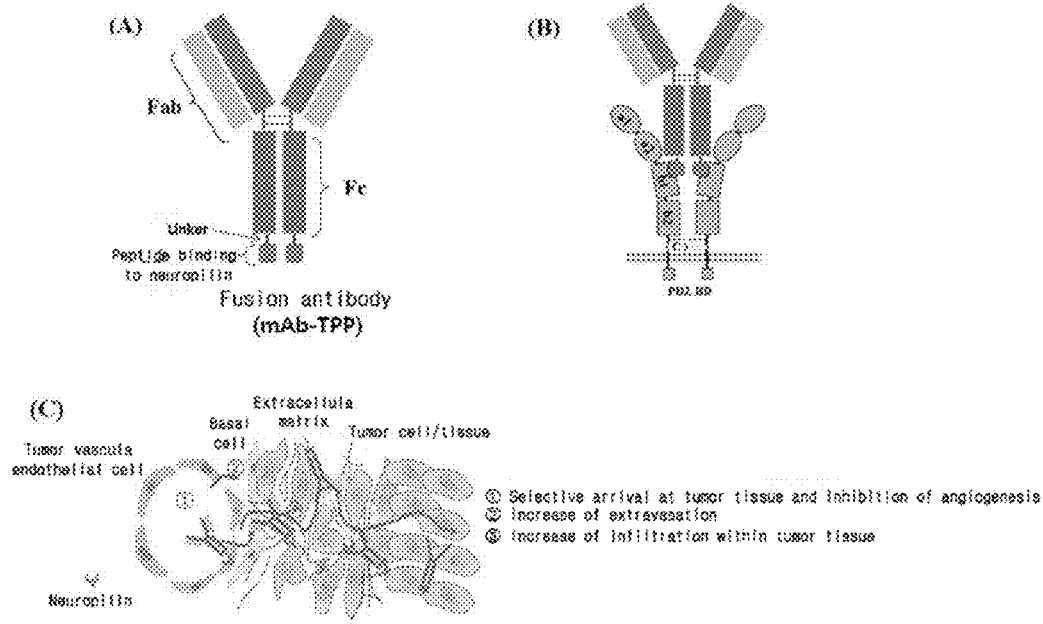
FIG. 13(A) is a schematic diagram illustrating a fusion antibody (mAb-TPP) where a peptide binding to neuropilin is linked by a peptide linker to heavy-chain constant region C-terminus of single clone antibody.
FIG. 13(B) is a schematic diagram illustrating that the fusion antibody of (A) binds to b1 domain of neuropilin-1 or -2.
FIG. 13(C) is a schematic diagram illustrating the mechanism expected when the above fusion antibody (mAb-TPP) is introduced into the body. The binding of peptide fused antibody to neuropilin-1 or -2 overexpressed in tumor vascular endothelium and various tumor cells increases selective distribution of tumor tissue, increases extravasation, and induces signal transduction increasing infiltration into tumor cells, which may result in remarkably increasing specific distribution of tumor tissue of fusion antibody and infiltration thereinto.

FIG. 13(A) is a schematic diagram illustrating a fusion antibody (mAb-TPP) where a peptide binding to neuropilin is linked by a peptide linker to C-terminus of a heavy chain constant region of single clone antibody. FIG. 13(B) illustrates a schematic diagram illustrating that the fusion antibody of (A) binds to b1 domain of neuropilin membrane protein. Further, FIG. 13(C) illustrates the mechanism expected when the fusion antibody (mAb-TPP) is introduced into the body. The peptide fused antibodies bind to overexpressed neuropilin membrane proteins of tumor endothelium and various tumor cells to ① increase selective distribution in tumor tissues, ② increase extravasation, and ③ induce signal transduction which increases infiltration into tumor tissues, thereby remarkably increasing tumor tissue specific distribution of fusion antibodies and infiltration into tumor tissues.

Figure 14:
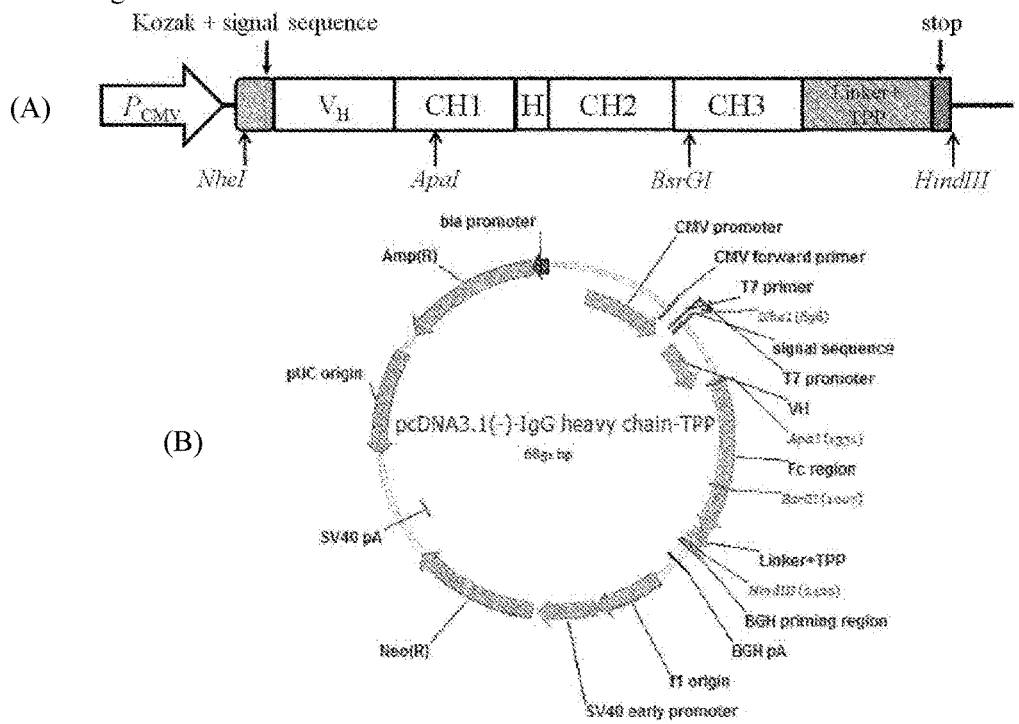
FIG. 14 is an example of a cleavage map of a vector for expressing IgG heavy chain-TPP.
Figure 15:
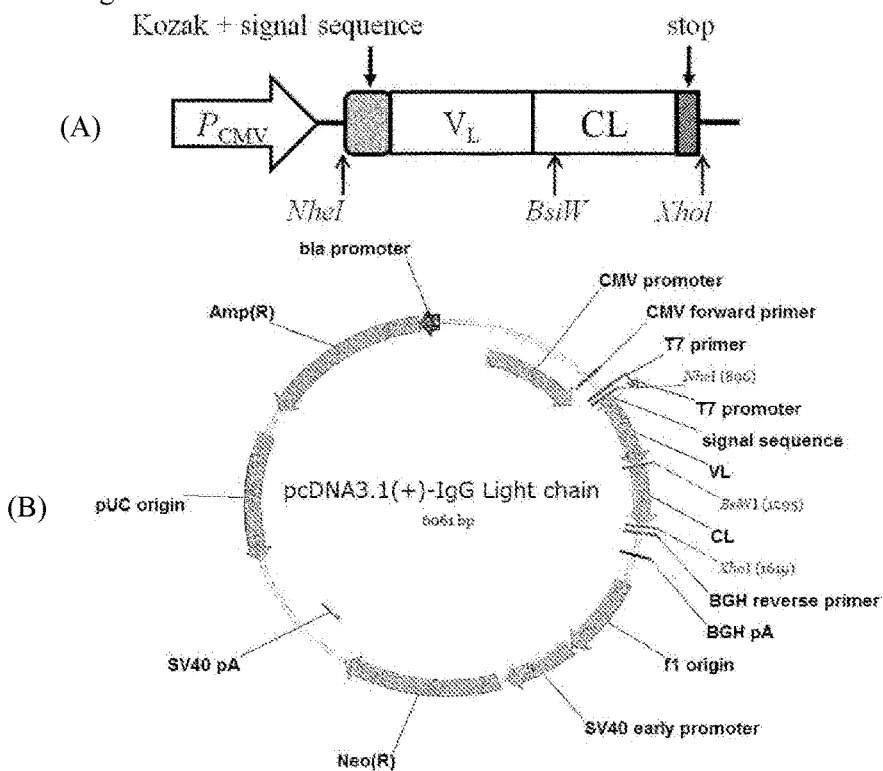
FIG. 15 is an example of a cleavage map of a vector for expressing IgG light chain in animal cells.

As a format for verifying the effect of TPP in mouse models, TPP fused Cetuximab and Trastuzumab were produced. TPP was fused to C-terminus of Fc of the existing anti-EGFR antibodies, Cetuximab IgG and Trastuzumab IgG. FIGS. 14 and 15 are maps of exemplary vectors for expressing IgG heavy chain-TPP and IgG light chain in host cells, respectively.

Figure 16:
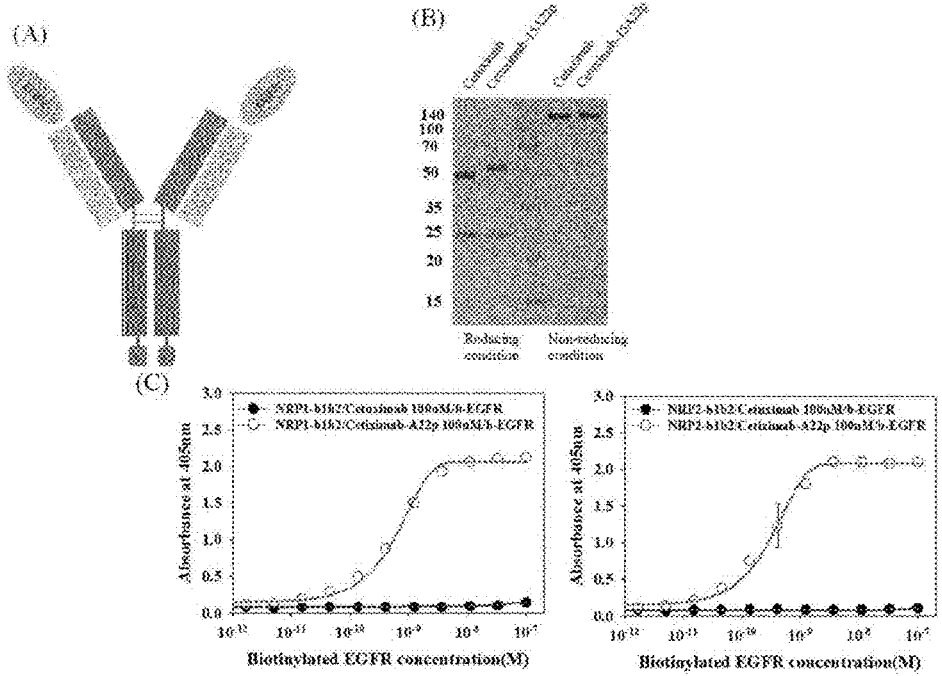
FIG. 16(A) is a schematic diagram illustrating an antibody constructed by introducing TPP into Fc C-terminus of Cetuximab IgG which is the existing anti-EGFR IgG.
FIG. 16(B) illustrates a result of analyzing the size and purity on SDS-PAGE under reducing and non-reducing conditions, after transient expression and purification in HEK293K cells through co-transformation.
FIG. 16(C) illustrates a result confirming through Sandwich ELISA that Cetuximab-TPP is capable of binding to antigen EGFR and neuropilin simultaneously.
Figure 17:
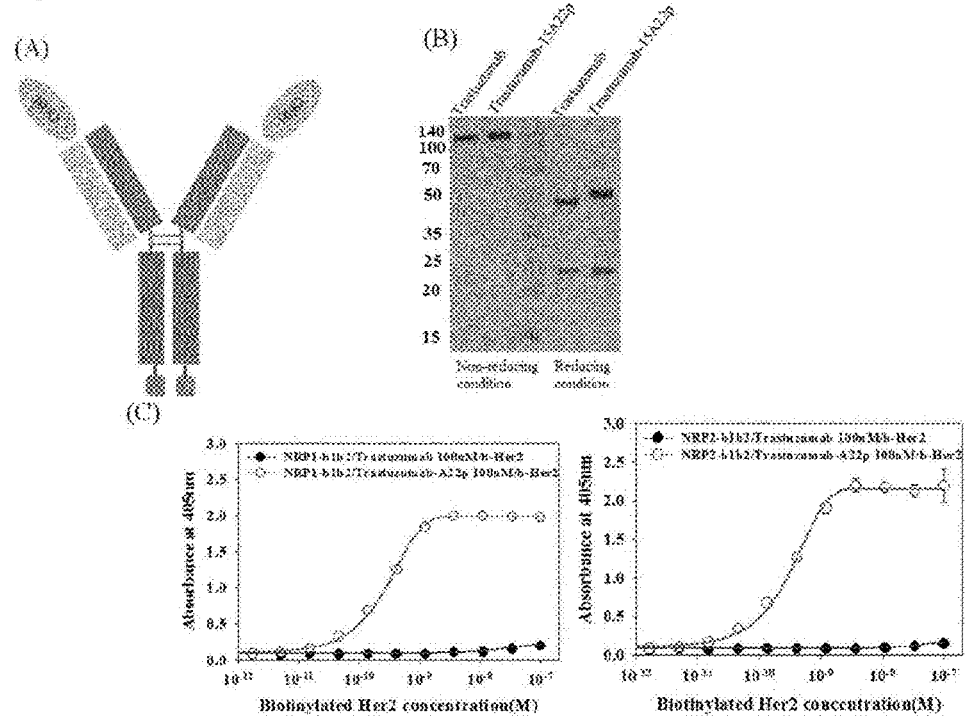
FIG. 17(A) is a schematic diagram illustrating an antibody introducing TPP into the existing anti-HER2 IgG Trastuzumab in the same manner as the experiment above.
FIG. 17(B) illustrates a result of analyzing the size and purity on SDS-PAGE under reducing and non-reducing conditions, after transient expression and purification in HEK293F cells through co-transformation.
FIG. 17(C) illustrates a result confirming through Sandwich ELISA that Trastuzumab-TPP is capable of binding to antigen Her2 and neuropilin simultaneously.

FIGS. 16(A) and 17(A) are schematic diagrams illustrating TPP fused antibodies. The expression and purification were performed in HEK293F in the same manner as in Example 4 above, and the purity was confirmed through SDS-PAGE. FIGS. 16(B) and 17(B) illustrate results of analyzing the size and purity on SDS-PAGE under reducing and non-reducing conditions, after transient expression and purification in HEK293F cells through co-transformation.

The following Table 8 shows the yield of proteins produced per 1 L culture of purified TPP fusion proteins. The results obtained from three times experiments were statistics processed, and ± represents standard deviation. The obtained yields of proteins (Cetuximab-15A22p and Trastuzumab-15A22p) are not remarkably different from those of wild-type proteins (Cetuximab and Trastuzumab).

TABLE 8

| Clone | Yield (mg/L culture) |
| --- | --- |
| Cetuximab | 39.9 ± 6.2 |
| Cetuximab-15A22p | 37.4 ± 4.7 |
| Trastuzumab | 113.6 ± 9.2 |
| Trastuzumab-15A22p | 105.8 ± 8.9 |

Comparison of Purification Yields Between TPP Fused Cetuximab and Trastuzumab (2) SPR Confirming Antigen Binding Capacity of mAb-TPP In order to confirm through surface plasmon resonance (SPR) whether mAb-TPP maintains binding affinity with antigen binding capacity of the existing antibodies, EGFR and Her2 in an amount of about 1000 RU were fixed on CM5 chips. The analysis was performed with HBS-EP buffer (10 mM Hepes, 3 mM ethylenediamine tetra acetic acid, and 0.005% surfactant P20 (pH 7.4), GE Healthcare) flowing at a rate of 30 μl/min. After bond and dissociation analysis, the regeneration of CM5 chip was performed by streaming a buffer (20 mM NaOH, 1 M NaCl, pH 10.0) at a stream velocity 30 μl/min for 1 minute. Each sensorgram obtained by 3 minute-bond and 3 minute-dissociation was normalized and subtracted by comparing with blank cells to calculate the binding affinity. The result is shown in Table 9. As shown in Table 9, the binding affinity of Cetuximab to EGFR was analyzed almost similarly as in other references, and the binding affinity of Cetuximab-TPP to EGFR was analyzed to be similar compared with Cetuximab. Also, the binding affinity of Trastuzumab to Her2 was analyzed almost similarly as in other references, and the binding affinity of Trastuzumab-TPP to Her2 was analyzed to be similar compared with Trastuzumab. It was confirmed that when TPP was fused to mAb, the fusion did not affect the existing antigen binding of the antibody. The analysis was performed using at least five sensorgrams, and the results obtained from two times experiments were statistics processed, and ± represents standard deviation of independent experimental results.

TABLE 9

| Clone | Receptors | Association rate ka ($M^{-1}s^{-1}$) | Dissociation rate kd ($S^{-1}$) | Binding affinity $K_D$(nM) |
|---|---|---|---|---|
| Cetuximab | EGFR | $6.24 \pm 0.17 \times 10^6$ | $1.50 \pm 0.35 \times 10^{-3}$ | $0.24 \pm 0.02$ |
| Cetuximab-15A22p | EGFR | $7.17 \pm 0.12 \times 10^6$ | $1.53 \pm 0.37 \times 10^{-3}$ | $0.21 \pm 0.01$ |
| Trastuzumab | Her2 | $7.90 \pm 0.07 \times 10^4$ | $1.06 \pm 0.14 \times 10^{-5}$ | $0.14 \pm 0.01$ |
| Trastuzumab-15A22p | Her2 | $8.45 \pm 0.31 \times 10^4$ | $1.67 \pm 0.37 \times 10^{-5}$ | $0.20 \pm 0.05$ |

Analysis Result of Binding Affinity of Cetuximab and Trastuzumab to EGFR and her2

(3) Sandwich ELISA for Confirming Bispecificity of mAb-TPP

Sandwich ELISA was performed to confirm bispecificity of mAb-TPP.

Specifically, 1 μg of each of b1b2 domains (273-586) of neuropilin-1 and b1b2 domain (275-595) of neuropilin-2 were bound at room temperature for 1 hour in 96-well EIA/RIA plates (COSTAR Corning In., USA), and then washed three times for 10 minutes with 0.1% PBST (0.1% Tween20, pH 7.4, 137 mM NaCl, 10 mM Phosphate, 2.7 mM KCl, SIGMA-ALDRICH co., USA). After binding for 1 hour with 5% skim milk (pH 7.4, 137 mM NaCl, 10 mM Phosphate, 2.7 mM KCl, SIGMA-ALDRICH co., USA), it was washed three times for 10 minutes with 0.1% PBST (0.1% Tween20, pH 7.4, 137 mM NaCl, 10 mM Phosphate, 2.7 mM KCl, SIGMA-ALDRICH co., USA). The mAb and mAb-TPP at a concentration of 100 nM were bound to b1b2 domains of neuropilin-1 and -2, and then washed three times for 10 minutes with 0.1% PBST (0.1% Tween20, pH 7.4, 137 mM NaCl, 10 mM Phosphate, 2.7 mM KCl, SIGMA-ALDRICH co., USA). The bionylated EGFR (SIGMA-ALDRICH co., USA) and Her2-ECD (R&D systems, Minneapolis, Minn.) were diluted to be 1 μM to 1 nM and bound in each well using the same manner as above, and then washed three times for 10 minutes with 0.1% PBST (0.1% Tween20, pH 7.4, 137 mM NaCl, 10 mM Phosphate, 2.7 mM KCl, SIGMA-ALDRICH co., USA). After binding to alkaline phosphatase (AP)-conjugated anti-human mAb (Sigma, USA) and reacting with pnitrophenyl palmitate (pNPP, SIGMA-ALDRICH co., USA), absorbance at 405 nm was quantified.

FIGS. 16(C) and 17(C) are results confirming from ELISA analysis the bispecificity of mAb-TPP which has binding capacity to neuropilin-1 or -2 and original antigens of mAb simultaneously.

(4) SPR for Confirming Binding Capacity of mAb-TPP to Fc Receptor

In order to confirm through surface plasmon resonance (SPR) whether mAb-TPP maintains binding capacity to Fc receptors of the existing antibodies, the affinity with FcγRIIa, FcγRIIIa, FcγRIIIb, and FcRn was analyzed. For FcγRIIa, FcγRIIIa, and FcγRIIIb, the same method as in Example 6 above was used. For FcRn, the wild-type antibodies have the properties of binding to FcRn only at pH 6.0, but not at pH 7.4. For affinity analysis, SPR was performed for FcRn of mAb and mAb-TPP under pH 6.0 condition. FcRn in an amount of about 1000 RU was fixed on CMS chips. The analysis was performed with PBST buffer (pH 6.0, 137 mM NaCl, 10 mM Phosphate, 2.7 mM KCl, 0.005% surfactant P20, SIGMA-ALDRICH co., USA) flowing at a rate of 30 μl/min. After bond and dissociation analysis, the regeneration of CMS chip was performed by streaming HBS-EP buffer (10 mM Hepes, 3 mM ethylenediamine tetra acetic acid, and 0.005% surfactant P20 (pH 8.0), GE Healthcare) at a stream velocity 30 μl/min for 1 minute. Each sensorgram obtained by 3 minute-bond and 3 minute-dissociation of mAb (Cetuximab, Trastuzumab) and mAb-TPP (Cetuximab-TPP, Trastuzumab-TPP) was normalized and subtracted by comparing with blank cells to calculate the binding affinity. The result is shown in Table 10.

Figure 18:
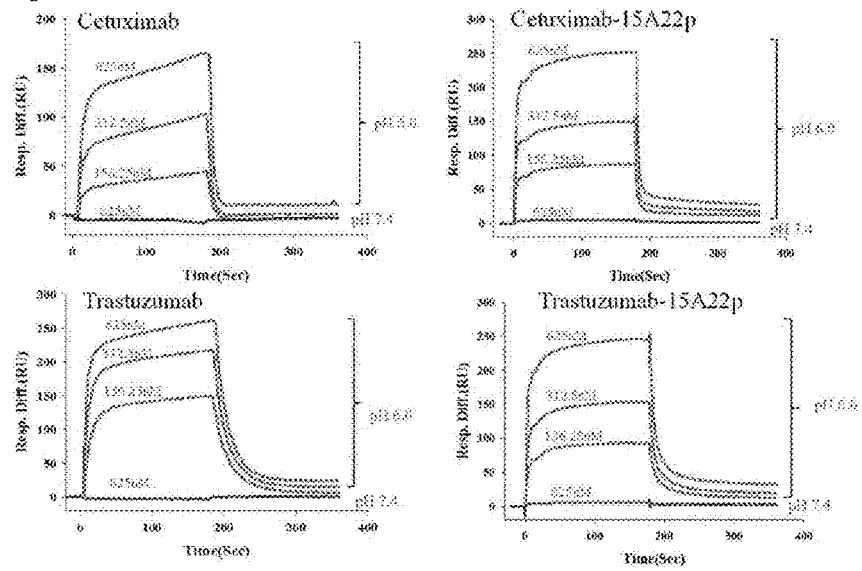
FIG. 18 illustrates a result of Surface Plasmon Resonance (SPR) for confirming whether binding capacity between mAb and mAb-TPP depending on pH for FcRn is similar to each other. It was proven that mAb (Cetuximab, Trastuzumab) showed a binding curve at pH 6.0, and mAb-TPP (Cetuximab-TPP, Trastuzumab-TPP) maintained the properties of wild-type antibodies which do not completely bind at pH 7.4.

The difference was confirmed in binding between this sensorgram and the sensorgram at the highest concentration 625 nM among the concentrations analyzed at pH 6.0 of the sensorgrams analyzed in Example 6 above. FIG. 18 illustrates a result confirming whether the binding capacities of mAb and mAb-TPP to FcRn are similar to each other depending on pH. As illustrated in FIG. 18, it was confirmed that all of mAb (Cetuximab, Trastuzumab) and mAb-TPP (Cetuximab-TPP, Trastuzumab-TPP) have the properties of binding to FcRn only at pH 6.0, but not at pH 7.4. Accordingly, it was confirmed that TPP fusion did not affect the binding capacity to Fc receptor.

TABLE 10

| Clone | Receptor | Association rate ka ($M^{-1}s^{-1}$) | Dissociation rate kd ($S^{-1}$) | Binding affinity $K_D$(M) |
|---|---|---|---|---|
| Cetuximab | FcRn (pH 6.0) | $8.27 \pm 0.60 \times 10^3$ | $4.28 \pm 0.16 \times 10^{-3}$ | $5.17 \pm 0.21 \times 10^{-7}$ |
| Cetuximab-15A22p | FcRn (pH 6.0) | $7.71 \pm 0.04 \times 10^3$ | $4.35 \pm 0.06 \times 10^{-4}$ | $5.64 \pm 0.10 \times 10^{-7}$ |
| Trastuzumab | FcRn (pH 6.0) | $3.24 \pm 0.07 \times 10^3$ | $1.49 \pm 0.14 \times 10^{-3}$ | $4.59 \pm 0.16 \times 10^{-7}$ |
| Trastuzumab-15A22p | FcRn (pH 6.0) | $7.23 \pm 0.30 \times 10^3$ | $3.72 \pm 0.31 \times 10^{-3}$ | $5.15 \pm 0.15 \times 10^{-7}$ |
| Cetuximab | FcγR IIa | $8.64 \pm 0.04 \times 10^3$ | $2.28 \pm 0.17 \times 10^{-3}$ | $2.64 \pm 0.14 \times 10^{-7}$ |

TABLE 10-continued

| Clone | Receptor | Association rate ka (M$^{-1}$s$^{-1}$) | Dissociation rate kd (S$^{-1}$) | Binding affinity K$_D$(M) |
|---|---|---|---|---|
| Cetuximab-15A22p | FcγR IIa | 1.40 ± 0.07 × 10$^4$ | 3.28 ± 0.14 × 10$^{-3}$ | 3.12 ± 0.16 × 10$^{-7}$ |
| Trastuzumab | FcγR IIa | 2.39 ± 0.20 × 10$^4$ | 5.04 ± 0.25 × 10$^{-3}$ | 2.11 ± 0.10 × 10$^{-7}$ |
| Trastuzumab-15A22p | FcγR IIa | 2.47 ± 0.17 × 10$^4$ | 7.98 ± 0.35 × 10$^{-3}$ | 3.23 ± 0.27 × 10$^{-7}$ |
| Cetuximab | FcγR IIIa | 1.94 ± 0.19 × 10$^4$ | 1.91 ± 0.20 × 10$^{-2}$ | 9.85 ± 0.12 × 10$^{-7}$ |
| Cetuximab-15A22p | FcγR IIIa | 1.98 ± 0.20 × 10$^4$ | 1.68 ± 0.25 × 10$^{-2}$ | 8.47 ± 0.21 × 10$^{-7}$ |
| Trastuzumab | FcγR IIIa | 1.61 ± 0.28 × 10$^4$ | 1.50 ± 0.20 × 10$^{-2}$ | 9.33 ± 0.85 × 10$^{-7}$ |
| Trastuzumab-15A22p | FcγR IIIa | 2.23 ± 0.28 × 10$^4$ | 2.09 ± 0.03 × 10$^{-2}$ | 9.38 ± 0.17 × 10$^{-7}$ |
| Cetuximab | FcγR IIIb | 5.10 ± 0.45 × 10$^3$ | 4.20 ± 0.19 × 10$^{-2}$ | 8.23 ± 0.14 × 10$^{-6}$ |
| Cetuximab-15A22p | FcγR IIIb | 1.57 ± 0.45 × 10$^3$ | 1.45 ± 0.20 × 10$^{-2}$ | 9.22 ± 0.22 × 10$^{-6}$ |
| Trastuzumab | FcγR IIIb | 5.30 ± 0.14 × 10$^3$ | 4.47 ± 0.22 × 10$^{-2}$ | 8.43 ± 0.33 × 10$^{-6}$ |
| Trastuzumab-15A22p | FcγR IIIb | 7.08 ± 0.43 × 10$^3$ | 6.66 ± 0.13 × 10$^{-2}$ | 9.39 ± 0.23 × 10$^{-6}$ |

Analysis of binding affinity KD values of IgG-TPP to Fc receptor

Example 12: Confirmation on Improvement of Infiltration Capacity of mAb-TPP into Tissue In order to confirm the infiltration of antibodies within tumor tissues by IgG-TPP constructed in the above experiments, 5×10$^6$ cells of each of FaDu and A431 were subcutaneously injected into Balb/c nude mice respectively, and when the volume of the tumor became about 300-400 mm$^3$ after about 9 days, 2.5 mg/kg of PBS, Cetuximab, and Cetuximab-15A22P were intravenously injected, respectively. After the injection, the tumor was extracted from the mice after 3 hours and 12 hours, respectively, and an immunohistochemistry experiment was performed. The tissue was stained and observed in the same manner as in Example 9.

Figure 19A:
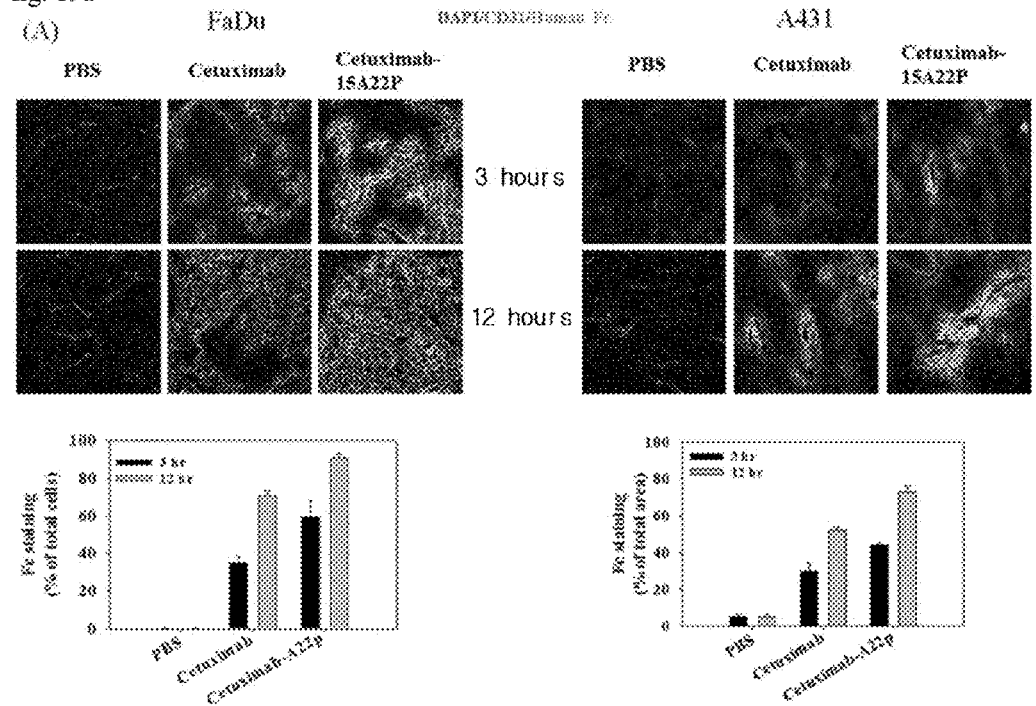
FIG. 19a illustrates a result of IHC for confirming the infiltration capacity of Cetuximab-TPP in tumor tissues. After transplanting into nude mice each of human head and neck cancer cell line FaDu and human epidermoid carcinoma A431 in which EGFR is expressed, Cetuximab and Cetuximab-15A22P were injected thereto to confirm infiltration capacity into tissue through double staining with blood vessels (CD31). As a result, it was confirmed that Cetuximab infiltrated into the periphery of blood vessels, whereas Cetuximab-15A22P infiltrated into the tissue to be further far away from blood vessels (upper panel). This was quantified using Image J (lower panel).

FIG. 19a illustrates a result of IHC for confirming the infiltration capacity of Cetuximab-TPP in tumor tissues. As illustrated in FIG. 19a, in the case of Cetuximab, green fluorescence was observed only around the blood vessels in the two cancer cell tissues of FaDu and A431. In comparison, it was confirmed that in the case of Cetuximab-15A22P, as compared to Cetuximab, Cetuximab-15A22P infiltrated into the tissue to be further away from the blood vessels. Also, the samples were compared after 3 hours and 12 hours, and accordingly it was confirmed that the cell infiltrates further into the tissue as time passes. ImageJ was used to quantify this.

Figure 19B:
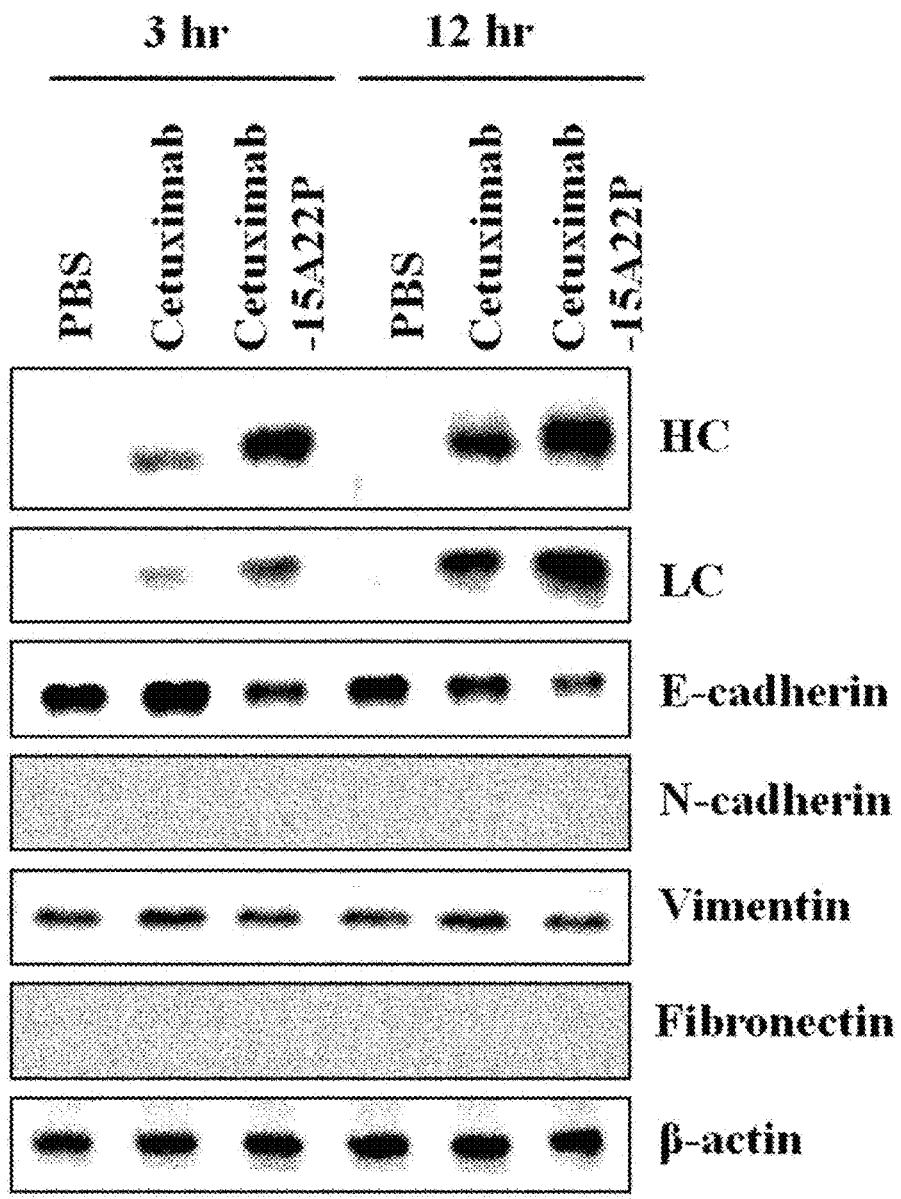
FIG. 19b illustrates a result of Western blot performed from cancer cell tissues extracted from mice under the conditions of FIG. 18b.

Further, Western blot was performed from the cancer cell tissue used in this condition, and the result is illustrated in FIG. 19b. As illustrated in FIG. 19b, when performing Western blot using antibodies recognizing the heavy chain site and light chain site of human antibody, respectively, it was confirmed that more amount of Cetuximab-15A22P was present in the tissue than Cetuximab. Also, it was confirmed that only E-cadherin was decreased by Cetuximab-TPP, and N-cadherin, vimentin, fibronetin, etc., which are proteins relating to metastasis of cancer cells, did not change. Unlike the metastasis of cancer cells accompanied by the decrease of E-cadherin and increase of N-cadherin, vimentin, fibronetin, etc., it was indirectly proved that metastasis and infiltration of cancer cells do not occur by the effect of TPP.

Also, in order to confirm whether such tendency actually affects inhibition of cancer cells, an experiment confirming the inhibition of cancer cell growth was performed in nude mice. In the same manner as Example 9, cell line FaDu was subcutaneously injected into nude mice, and after about 5 days from transplanting cells, when the volume of the tumor became about 120 mm$^3$, Cetuximab and Cetuximab-15A22P were intravenously injected 6 times every 3 days in an amount of 2.5 and 10 mg/kg (N=6).

Figure 19C:
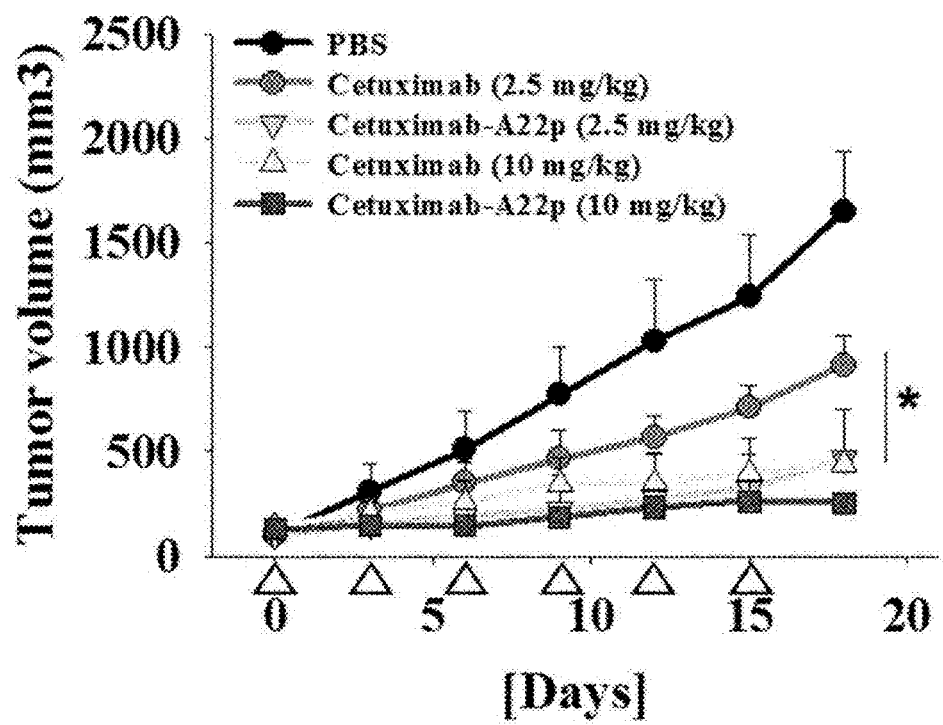
FIG. 19c illustrates a result of experiment on inhibition of cancer cell growth in nude mice for confirming whether improved infiltration into tumor tissue actually affects inhibition of cancer cell. As a result, it was confirmed that Cetuximab and Cetuximab-15A22P inhibited the growth of cancer cell, compared with PBS, and that Cetuximab-15A22P more effectively inhibited the growth of cancer cell under the same conditions.
Figure 19D:
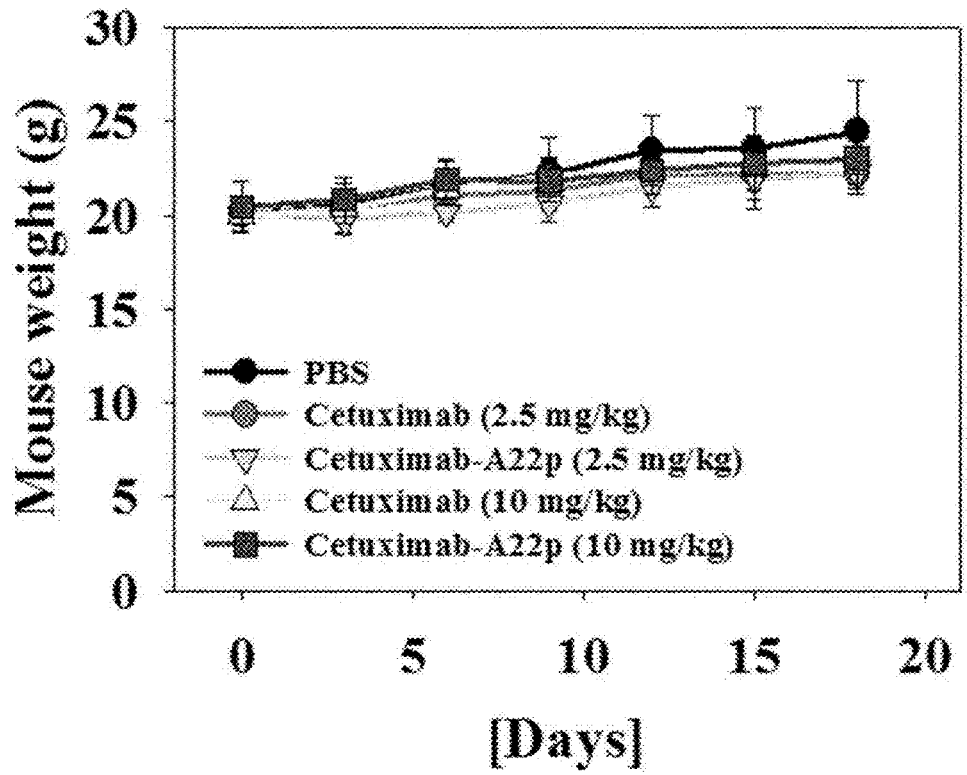
FIG. 19d illustrates a result of measuring the weights of mice at the time of conducting the above experiment. When compared with the experimental group into which Cetuximab was injected, the experimental group mice into which Cetuximab-15A22P was injected had no difference in weight. This indirectly proves that Cetuximab-15A22P does not have any toxicity against mice, compared with Cetuximab.

As illustrated in FIG. 19c, as compared to the control group PBS, it was confirmed that Cetuximab (CTX) and Cetuximab-15A22P inhibited cancer cell growth, and that Cetuximab-15A22P inhibited it more effectively than Cetuximab. Also, as illustrated in FIG. 19d, it was confirmed that the experimental group Cetuximab-15A22P did not present a great difference in weight as compared with the experimental group Cetuximab, and accordingly, it is determined to have no toxicity.

In the same manner as the above test, an IHC experiment was performed to confirm the antibody infiltrated into tumor tissue using the constructed Trastuzumab-15A22P. 5×10$^6$ cells of SK-OV-3 were subcutaneously injected into Balb/c nude mice, respectively, and when the volume of the tumor became about 300-400 mm$^3$ after about 9 days, 2.5 mg/kg of PBS, Trastuzumab and Trastuzumab-15A22P were intravenously injected, respectively. After the injection, the tumor was extracted from the mice after 3 hours and 12 hours, respectively, and an immunohistochemistry experiment was performed. The tissue was stained and observed in the same manner as the experiment above.

FIG. 20a illustrates a result of IHC for confirming the infiltration capacity of Trastuzumab-TPP in tumor tissues. As illustrated in FIG. 20a, in the case of Trastuzumab, green fluorescence was observed only around the blood vessels. In comparison, in the case of Trastuzumab-15A22P, as compared to Trastuzumab, it is confirmed that Trastuzumab-15A22P infiltrated into the tissue to be further away from the blood vessels. Also, the samples were compared after 3 hours and 12 hours, and accordingly it was confirmed that the cell infiltrates further into the tissue as time passes. ImageJ was used to quantify this.

Further, Western blot was performed from the cancer cell tissue used in this condition, and the result is illustrated in FIG. 20b. As illustrated in FIG. 20b, when performing Western blot using antibodies recognizing the heavy chain site and light chain site of human antibody, respectively, it was confirmed that more amount of Trastuzumab-15A22P was present in the tissue than Trastuzumab. Also, it was confirmed that only E-cadherin was decreased by Trastuzumab-TPP, and N-cadherin, vimentin, fibronetin, etc., which are proteins relating to metastasis of cancer cells, did not change. Through this, it was indirectly proved that metastasis and infiltration of cancer cells do not occur by the effect of TPP.

Figure 20C:
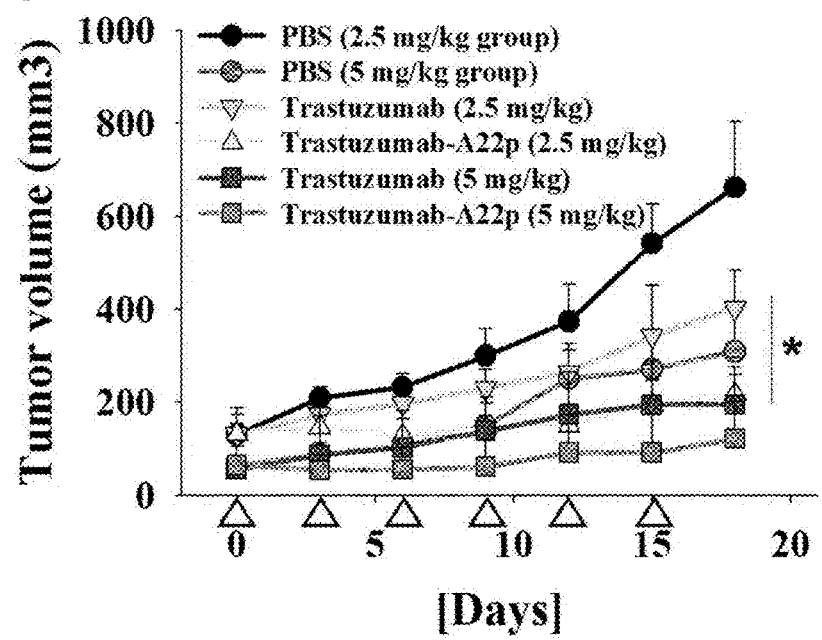
FIG. 20c illustrates a result of experiments for confirming the effect of Trastuzumab-TPP on inhibiting the growth of cancer cell. As a result, it was confirmed that under the same conditions, Trastuzumab-15A22P more effectively induced inhibition on the growth of cancer cell than Trastuzumab.
Figure 20D:
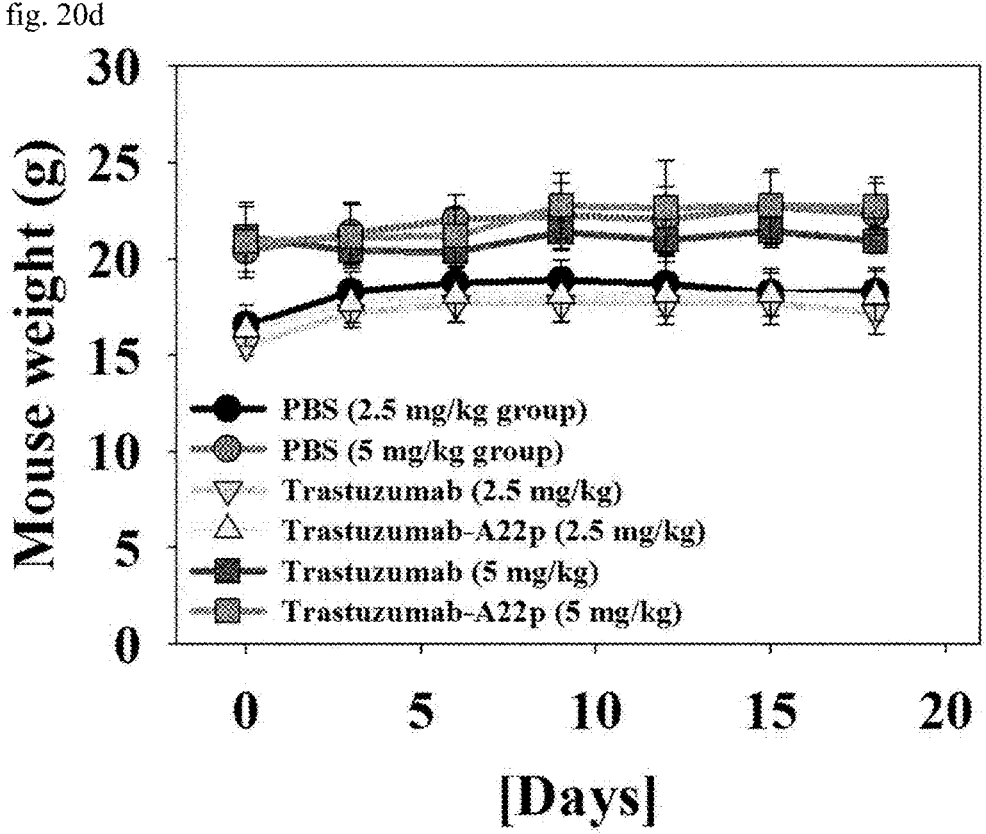
FIG. 20d illustrates a result of measuring weights of mice during the above experiments. When compared with mice of the experimental group into which Trastuzumab was injected, mice of the experimental group into which Trastuzumab-15A22P was injected had no difference in weights. This indirectly proved that Trastuzumab-15A22P did not have any toxicity against mice, when compared with Trastuzumab.

In the same manner as the above experiment, in order to confirm the effect of cancer cell growth inhibition of Trastuzumab-TPP, 5×10$^6$ cells of SK-OV-3 were subcutaneously injected into nude mice, respectively, and when the volume of the tumor became about 80 mm$^3$ after about 7 days from transplanting the cells, Trastuzumab and Trastuzumab-15A22P were intravenously injected 6 times every 3 days in an amount of 2.5 and 5 mg/kg (N=6). FIG. 20c illustrates a result of measuring the volume of the tumor to confirm the effect of Trastuzumab-TPP to inhibit cancer cell growth. As illustrated in FIG. 20c, it was confirmed that Trastuzumab-15A22P induced inhibition of cancer cell growth more effectively than Trastuzumab. FIG. 20d illustrates a result of measuring the weight of mice during the experiment. As illustrated in FIG. 20d, it can be understood that the experimental group Trastuzumab-15A22P did not present a great difference in weight as compared with the experimental group Trastuzumab, and it is determined to have no toxicity.

The results show that tumor tissue-penetrating A22p peptide may be generally applied to various monoclonal antibodies recognizing various antigens.

Example 13: Evaluation on Cytotoxicity of Fc-TPP and mAb-TPP

As a result, it is confirmed that improvement of infiltration capacity of TPP in tissue inhibits the growth of cancer cells in mice. In order to confirm whether the TPP itself has cytotoxicity in vitro, the cell lines used in the experiments above, FaDu and SK-OV-3, are treated with Fc-TPP and mAb-TPP, respectively, and the degree of cell growth inhibition was evaluated.

Particularly, $1 \times 10^4$ cells (FaDu, SK-OV-3) were diluted in 0.5 ml of a medium including 10% FBS per well in 24-well plate, respectively, and cultured. When the cells were stabilized, they were treated with 1 μM of Fc, Fc-15A22P, mAb, and mAb-15A22P, and observed for 72 hours, and then the number of cells alive was counted to compare the degree of cell growth. The effect was confirmed by treating cell line FaDu with Fc, Fc-15A22P, Cetuximab, and Cetuximab-15A22P, and treating SK-OV-3 with Fc, Fc-15A22P, Trastuzumab, and Trastuzumab-15A22P.

Figure 21:
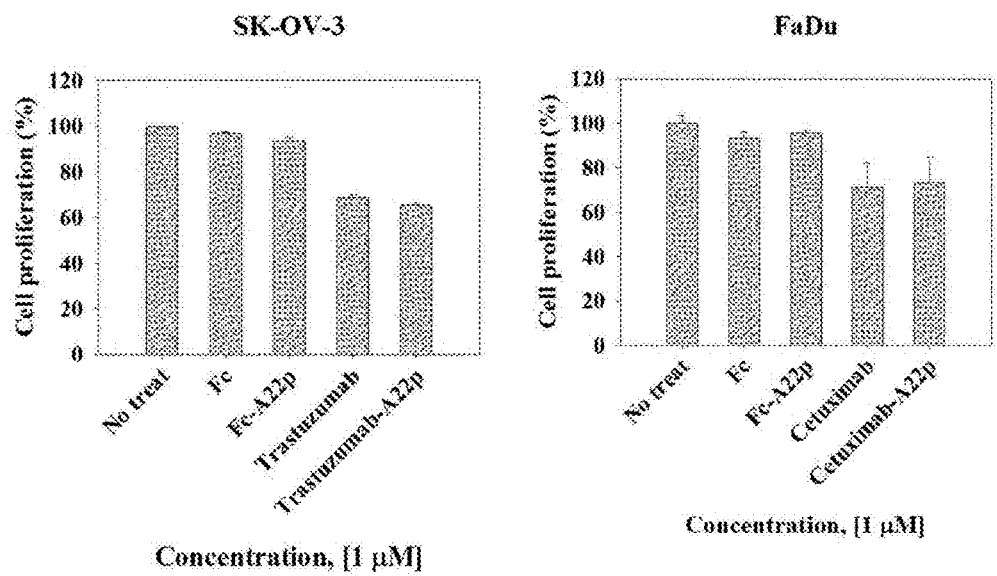
FIG. 21 illustrates a result of in vitro evaluation on the degree of cell growth inhibition by treating human head and neck cancer cell line FaDu and human ovarian cancer cell line SK-OV-3 with Fc-TPP and mAb-TPP. As a result, Cetuximab and Cetuximab-15A22P inhibited cell growth by about 30% in cell line FaDu, and Trastuzumab and Trastuzumab-15A22P inhibited cell growth by about 30-35% in cell line SK-OV-3. It was confirmed that there was no difference between mAb and mAb-TPP. Likewise, Fc and Fc-TPP did not show an effect of inhibiting cell growth in both FaDu and SK-OV-3. The mechanism of TPP by neuropilin means that TPP itself maximizes the effect by increasing infiltration into tumor tissue without directly affecting the growth of cancer cells.

FIG. 21 illustrates a result of in vitro evaluation on the degree of cell growth inhibition by treating FaDu and SK-OV-3 with Fc-TPP and mAb-TPP. As illustrated in FIG. 21, Cetuximab and Cetuximab-15A22P inhibited cell growth by about 30% in cell line FaDu, and Trastuzumab and Trastuzumab-15A22P inhibited cell growth by about 30-35% in cell line SK-OV-3. It was confirmed that there was no difference between the mAb and mAb-TPP. Likewise, Fc and Fc-TPP did not inhibit cell growth in both FaDu and SK-OV-3. This means that with regard to the effect of TPP by neuropilin, TPP maximizes the effect by increasing infiltration into tumor tissue without directly affecting the growth of cancer cells. Also, it was indirectly confirmed that the effect of mAb-TPP confirmed through the above test is not an effect by the interaction between EGFR and neuropilin, and between HER2 and neuropilin.

MODES FOR CARRYING OUT THE INVENTION

An aspect of the present invention provides a tumor tissue-penetrating peptide (TPP) specifically binding to neuropilin.

The tumor tissue-penetrating property in the above aspect means, for example, having any one of the properties of 1) specifically recognizing a tumor specific vascular endothelial cell, a tumor cell or tissue and accumulating in it, 2) widening intercellular gaps between tumor vascular endothelial cells and promoting extravasation, and 3) controlling intercellular gap between tumors within the tumor and increasing infiltration within the tumor.

The term neuropilin (NRP) as used herein is a transmembrane glycoprotein, and there are two forms of neuropilin, NRP1 and NRP2. The structures of NRP1 and NRP2 are as illustrated in FIGS. 1 (D) and (E). Neuropilin broadly consists of five domains, and from the N-terminus, a1 and a2 domains are classified as CUB domains, and an Ig-like C2 type of semaphorin binds thereto. Particularly, this site forms a complex with plexin, and plays a role of increasing the binding force with semaphorin-plexin. The b1 and b2 domains of neuropilin are classified as FV/VIII domains, and the C-terminus of VEGF family ligand or secreted class 3 semaphorin ligands (secreted Sema3s) binds thereto. The VEGF ligand and Sema3s have a site recognizing furin hydrolysis enzymes (RXRR, Arg-Xaa-Arg-Arg) (SEQ ID NO: 13), and thus they commonly end with an arginine (Arg) amino acid residue at the C-terminus by Furin processing (Adams et al. 1997). It has been reported that the C-terminus Arg residues of VEGF ligand and Sema3s are very important in the interaction between b1 and b2 domains of neuropilin (Teesalu et al. 2009). The tertiary structure of the complex of VEGF ligand and b1b2 domains of neuropilin has been revealed (Parker et al., 2012), and accordingly the amino acid sequence of VEGF important in the binding to the b1b2 domains of neuropilin may be known. However, for Sema3A binding to NRP1 and Sema3F binding to NRP2, it still has not been found out which site of the C-terminus of these ligands specifically bind to NRP.

The tumor tissue-penetrating peptide represented by an amino acid sequence selected from the group consisting of SEQ ID NO: 1 to SEQ ID NO: 4 is a peptide designed based on the similarity of the C-terminus sequences by analyzing the sequence of the VEGF165A and the furin C-terminus sequence of semaphorin 3A and semaphorin 3F known to bind to neuropilin, by analyzing the amino acid sequence and length of the binding site of VEGF165A ligand binding to b1b2 domains of neuropilin.

A22, which is a tumor tissue-penetrating peptide represented by an amino acid sequence of SEQ ID NO:1, is a peptide consisting of 22 amino acids derived from residues 739-760, which are part of the basic domain of semaphorin 3A. A22p, which is a tumor tissue-penetrating peptide represented by an amino acid sequence of SEQ ID NO: 2, transforms the third amino acid from the C-terminus of A22, which is the 758th asparagine (Asn758), to proline (Pro, P) (Asn758Pro). F22, which is a tumor tissue-penetrating peptide represented by an amino acid sequence of SEQ ID NO: 3, is a peptide consisting of 22 amino acids derived from residues 758-779, which are part of the basic domain of semaphorin 3F. F22p, which is a tumor tissue-penetrating peptide represented by an amino acid sequence of SEQ ID NO: 4, transforms the third amino acid from the C-terminus of F22, which is the 777th asparagine (Asn777), to proline (Pro, P) (Asn777Pro). The peptides A22p and F22p are designed to derive peptides with improved affinity with neuropilin by inserting mutants to Sema3A- and Sema3F-derived peptides.

The name of the peptide of the present invention, semaphorin-derived sequence and SEQ ID NO. are as shown below.

| TPP name | Ligand derived | Entire amino acid sequence from N-terminus to C-terminus) | SEQ ID NO. |
|---|---|---|---|
| A22 | Semaphorin 3A | HTPGNSNKWKHLQENKKGRNRR | SEQ ID NO: 1 |
| A22p | Semaphorin 3A | HTPGNSNKWKHLQENKKGRPRR | SEQ ID NO: 2 |
| F22 | Smephorin 3F | REAPGAPRSPEPQDQKKPRNRR | SEQ ID NO: 3 |
| F22p | Semaphorin 3F | REAPGAPRSPEPQDQKKPRPRR | SEQ ID NO: 4 |

The tumor tissue-penetrating peptide of the above aspect may further include a linker peptide. The linker peptide may consist of 1 to 50 amino acids, preferably 4 to 20 amino acids, and more preferably 4 to 15 amino acids. Also, the linker peptide may consist of glycine, serine or alanine, preferably the sequence of the linker peptide may consist of an amino acid sequence of (GA)n or (GGGGS)m (wherein n and m are each independently an integer between 1 and 20), and more preferably may consist of an amino acid sequence of GAGA (SEQ ID NO: 11) or (GGGGS)3 (SEQ ID NO: 12).

The tumor targeting capacity is confirmed in various combinations of the linker and semaphorin-derived sequence in a detailed embodiment of the present invention. The name of peptide, sequence of linker, semaphorin-derived sequence, length of entire amino acid and SEQ ID NO. are as shown below.

| TPP Name | Linker sequence | Neuropilin target sequence | Length of entire amino acid | SEQ ID NO. |
|---|---|---|---|---|
| 4A22 | GAGA | HTPGNSNKWKHLQENKKGRNRR (SEQ ID NO: 1) | 26 | SEQ ID NO: 5 |
| 15A22 | GGGGSGGGGSGGGGS | HTPGNSNKWKHLQENKKGRNRR (SEQ ID NO: 1) | 37 | SEQ ID NO: 6 |
| 15A22p | GGGGSGGGGSGGGGS | HTPGNSNKWKHLQENKKGRPRR (SEQ ID NO: 2) | 37 | SEQ ID NO: 7 |
| 4F22 | GAGA | REAPGAPRSPEPQDQKKPRNRR (SEQ ID NO: 3) | 26 | SEQ ID NO: 8 |
| 13F22 | GGGGSGGGGSGGGGS | REAPGAPRSPEPQDQKKPRNRR (SEQ ID NO: 3) | 37 | SEQ ID NO: 9 |
| 15F22p | GGGGSGGGGSGGGGS | REAPGAPRSPEPQDQKKPRPRR (SEQ ID NO: 4) | 37 | SEQ ID NO: 10 |

(In the table, GAGA is SEQ ID NO: 11 and GGGGSGGGGSGGGGS is SEQ ID NO: 12.)

Another aspect of the present invention provides a fusion protein, a nanoparticle or a liposome having the tumor tissue-penetrating peptide fused therein.

The protein may be antibodies, antibody fragments, immuoglobulin, peptides, enzymes, transcription factors, toxins, antigen peptides, hormones, carrier proteins, structural proteins, motor function proteins, receptors, signaling proteins, storage proteins, membrane proteins, transmembrane proteins, internal proteins, external proteins, secretory proteins, viral proteins, native proteins, glycoproteins, cleaved proteins, proteins with disulfide bond, protein complexes, chemically modified proteins, or prions, etc.

According to the present invention, liposomes include at least one lipid bilayer enclosing the inner aqueous compartment, which is capable of being associated by itself Liposomes may be characterized by membrane type and size thereof. Small unilamellar vesicles (SUVs) may have a single membrane and may range between 20 and 50 nm in diameter. Large unilamellar vesicles (LUVs) may be at least 50 nm in diameter. Oliglamellar large vesicles and multilamellar large vesicles may have multiple, usually concentric, membrane layers and may be at least 100 nm in diameter. Liposomes with several nonconcentric membranes, i.e., several small vesicles contained within a larger vesicle, are referred to as multivesicular vesicles.

According to the present invention, a nanoparticle refers to a particle including substances ranging between 1 and 1,000 nm in diameter. The nanoparticle may be a metal nanoparticle, a metal/metal core shell complex consisting of a metal nanoparticle core and a metal shell enclosing the core, a metal/non-metal core shell consisting of a metal nanoparticle core and a non-metal shell enclosing the core, or a non-metal/metal core shell complex consisting of a non-metal nanoparticle core and a metal shell enclosing the core. According to an embodiment, the metal may be selected from gold, silver, copper, aluminium, nickel, palladium, platinum, magnetic iron and oxides thereof, but is not limited thereto, and the non-metal may be selected from silica, polystyrene, latex and acrylate type substances, but is not limited thereto.

Also, the tumor tissue-penetrating peptide may have at least a bivalent binding to neuropilin.

According to the present invention, fusion refers to unifying two molecules having the same or different function or structure, and the methods of fusing include any physical, chemical or biological method binding the tumor tissue-penetrating peptide to the protein, nanoparticle or liposome. Preferably, the fusion may be made by a linker peptide, and for example, the linker peptide may bind to C-terminus of Fc fragment of an antibody.

In the present invention, a complete antibody has a structure with two full-length light chains and two full-length heavy chains, and each light chain is linked to each heavy chain by a disulfide bond (SS-bond). A constant region of the antibody is divided into a heavy-chain constant region and a light-chain constant region, and the heavy-chain constant region has γ, μ, α, δ and ε types, and γ1, γ2, γ3, γ4, α1 and α2 subclasses. The light-chain constant region has κ and λ types.

The term "heavy chain" as used herein may be interpreted to include a full-length heavy chain including variable region domain VH including an amino acid sequence having a variable region sequence sufficient to confer antigen-specificity and three constant region domains CH1, CH2 and CH3, and a fragment thereof. Also, the term "light chain" as used herein may be interpreted to include a full-length light chain including a variable region domain VL including an amino acid sequence having a variable region sequence sufficient to confer antigen-specificity and constant region domain CL, and a fragment thereof.

According to the present invention, a fragment of an antibody refers to each domain of a heavy chain or a light chain of an antibody, or a fragment thereof. For example, it may be a heavy-chain constant region, a heavy-chain variable region, a light-chain constant region, or a light-chain variable region of an antibody, or a fragment thereof. Preferably, the fragment of the antibody may be a heavy-chain constant region of an antibody.

Also, the fragment of the antibody may be a monomer, a dimer or a polymer.

The antibody includes monoclonal antibodies, non-specific antibodies, non-human antibodies, human antibodies, humanized antibodies, chimeric antibodies, single-chain Fvs (scFV), single chain antibodies, Fab fragments, F(ab') fragments, disulfide-linked Fvs (sdFV) and anti-idiotype (anti-Id) antibodies, and epitope-binding fragments of these antibodies, but is not limited thereto.

The monoclonal antibody may be IgG, IgM, IgA, IgD or IgE. For example, the monoclonal antibody may be IgG1, IgG2, IgG3, IgG4, IgM, IgE, IgA1, IgA5, or IgD type, and may be IgG1. Also, the light-chain constant region of the antibody may be λ or κ type.

The peptide may bind to a heavy-chain constant region (Fc) fragment of an antibody, preferably to the C-terminus of a heavy-chain constant region (Fc) fragment of an antibody, and the binding may be formed by a linker peptide.

Also, another aspect of the present invention provides a polynucleotide coding a peptide represented by an amino acid sequence selected from the group consisting of SEQ ID NO:1 to SEQ ID NO: 10.

The term "polynucleotide" as used herein refers to a deoxyribonucleotide or ribonucleotide polymer present in single-stranded or double-stranded form. It includes RNA genome sequence, DNA (gDNA and cDNA), and RNA sequence transcribed therefrom. Unless otherwise described, it also includes an analog of the natural polynucleotide.

The polynucleotide includes not only a nucleotide sequence coding an amino acid sequence of any one of SEQ ID NO: 1 to SEQ ID NO: 10, but also a complementary sequence thereto. The complementary sequence includes a sequence fully complementary and a sequence substantially complementary. For example, this means a sequence that may be hybridized with a nucleotide sequence coding an amino acid sequence of any one of SEQ ID NO:1 to SEQ ID NO: 10 under stringent conditions known in the pertinent art.

Also, the polynucleotide may be modified. The modification includes the addition, deletion, or non-conservative substitution or conservative substitution of nucleotides. The polynucleotide coding the amino acid sequence is interpreted to include a nucleotide sequence that has substantial identity to the nucleotide sequence. The substantial identity may refer to a sequence having at least 80% sequence identity, at least 90% sequence identity, or at least 95% sequence identity when aligning the nucleotide sequence to correspond to any other sequence as much as possible and analyzing the aligned sequence using an algorithm generally used in the pertinent art.

Another aspect of the present invention provides a recombinant vector including the polynucleotide.

The term "vector" as used herein refers to a means for expressing a target gene in a host cell. For example, the vector may include plasmid vector, cosmid vector, bacteriophage vector, and virus vectors such as adenovirus vector, retrovirus vector, and adeno-associated virus vector. The vector that may be used as the recombinant vector may be produced by operating plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19, etc.), phages (for example, λgt4λB, λ-Charon, λΔz1 and M13, etc.), or virus (for example, CMV, SV40, etc.) commonly used in the pertinent art.

A polynucleotide coding an amino acid sequence of any one of SEQ ID NO: 1 to SEQ ID NO: 10 in the recombinant vector may be operatively linked to a promoter. The term "operatively linked" as used herein means a functional linkage between a nucleotide expression control sequence (such as a promoter sequence) and a second nucleotide sequence. Accordingly, the control sequence may control the transcription and/or translation of the second nucleotide sequence.

The recombinant vector may be generally constructed as a vector for cloning or a vector for expression. As the vector for expression, vectors generally used for expressing foreign protein from plants, animals or microorganisms in the pertinent art may be used. The recombinant vector may be constructed by various methods known in the pertinent art.

The recombinant vector may be constructed to be a vector that employs a prokaryotic cell or an eukaryotic cell as a host. For example, when the vector used is an expression vector and employs a prokaryotic cell as a host, the vector generally includes a strong promoter which may promote transcription (for example, pLλ promoter, trp promoter, lac promoter, tac promoter, T7 promoter, etc.), a ribosome binding site for initiation of translation, and termination sequences for transcription/translation. When the vector employs an eukaryotic cell as a host, a replication origin operating in the eukaryotic cell included in the vector may include an fl replication origin, an SV40 replication origin, a pMB1 replication origin, an adeno replication origin, an AAV replication origin, a CMV replication origin and a BBV replication origin, etc., but is not limited thereto. In addition, a promoter derived from a genome of a mammal cell (for example, a metalthionine promoter) or a promoter derived from a virus of a mammal cell (for example, an adenovirus anaphase promoter, a vaccinia virus 7.5K promoter, a SV40 promoter, a cytomegalo virus (CMV) promoter, or a tk promoter of HSV) may be used, and the promoter generally has a polyadenylated sequence as a transcription termination sequence.

Meanwhile, in addition to the tumor tissue-penetrating peptide of the present invention, the vector may express an antibody having the peptide fused therein or a fragment thereof. In the case of an antibody having the peptide fused therein or a fragment thereof, the vector may use both a vector system expressing a peptide and an antibody or fragment thereof simultaneously in one vector, or a vector system expressing them in separate vectors. For the latter, the two vectors may be introduced into the host cell through co-transformation and targeted transformation.

For example, the recombinant vector of the present invention may have the cleavage map illustrated in FIG. 4(B) or FIG. 13(B).

Another aspect of the present invention provides a host cell transformed with the recombinant vector.

Any kind of host cell known in the pertinent art may be used as a host cell. Examples of a prokaryotic cell include strains belonging to the genus *Bascillus* such as *E. coli* JM109, *E. coli* BL21, *E. coli* RR1, *E. coli* LE392, *E. coli* B, *E. coli* X 1776, *E. coli* W3110, *Bascillus subtilus* and *Bascillus thuringiensis, Salmonella typhimurium*, intestinal flora and strains such as *Serratia marcescens* and various *Pseudomonas* Spp., etc. In addition, when the vector is transformed in an eukaryotic cell, a host cell such as *Saccharomyce cerevisiae*, an insect cell, a plant cell, and an animal cell, for example, SP2/0, CHO (Chinese hamster ovary) K1, CHO DG44, PER.C6, W138, BHK, COS-7, 293, HepG2, Huh7, 3T3, RIN, and MDCK cell line, etc., may be used.

Another aspect of the present invention provides a method for preparing a tumor tissue-penetrating peptide, including culturing the host cell.

The polynucleotide or a recombinant vector including the same may be inserted into a host cell using an insertion method well known in the pertinent art. For example, when a host cell is a prokaryotic cell, the transfer may be carried out according to $CaCl_2$ method or an electroporation method, etc., and when a host cell is an eukaryotic cell, the vector may be transferred into a host cell according to a microscope injection method, calcium phosphate precipitation method, an electroporation method, a liposome-mediated transformation method, and a gene bombardment method, etc., but the transferring method is not limited thereto. When using microorganisms such as *E. coli*, etc. the product ability is higher than using animal cells. However, although it is not suitable for production of intact Ig form of antibodies due to glycosylation, it may be used for production of antigen binding fragments such as Fab and Fv.

The method for selecting the transformed host cell may be readily carried out according to a method well known in the pertinent art using a phenotype expressed by a selected label. For example, when the selected label is a specific antibiotic resistance gene, the transformant may be readily selected by culturing the transformant in a medium containing the antibiotic.

The aspect is a concept including the preparation of a tumor tissue-penetrating peptide (TPP), and an antibody having the peptide fused therein or a fragment thereof.

An example of a method for preparing a heavy-chain constant region (Fc) fragment of an antibody having a tumor tissue-penetrating peptide (TPP) fused therein is as shown below:

1) having the TPP fused in a heavy-chain constant region (Fc) fragment of an antibody starting from a hinge of an antibody and preparing a recombinant TPP fused heavy-chain constant region (Fc-TPP) expression vector cloning nucleic acids of (hinge)-CH2-CH3-linker-TPP;

2) transforming the prepared expression vector in a cell and expressing recombinant Fc-TPP protein; and 3) purifying and collecting the expressed recombinant Fc-TPP protein.

Also, an example of a method for preparing an antibody having a tumor tissue-penetrating peptide fused therein is as shown below:

1) preparing a heavy-chain site of recombinant TPP fused IgG cloning nucleic acids of VH-CH1-hinge-CH2-CH3-linker-TPP and a light-chain site vector of an antibody cloning nucleic acids of VL-CL of the prepared IgG-TPP;

2) co-transforming the prepared heavy-chain and light-chain expression vectors in a cell, and expressing recombinant IgG-TPP protein; and 3) purifying and collecting the expressed recombinant IgG-TPP protein.

Also, an aspect of the present invention provides a composition for treating or preventing cancer or angiogenesis-related diseases, including the tumor tissue-penetrating peptide, or a fusion protein, a small molecule drug, a nanoparticle, or a liposome having the peptide fused therein.

The tumor tissue-penetrating peptide of the present invention specifically binds to neuropilin, thereby being specifically distributed in tumors, and exhibiting efficacy to penetrate into tumors. Also, a specific part is substituted with a sequence of vascular endothelial growth factor A (VEGF165A), thereby maintaining tumor infiltration effect and remarkably improving affinity to neuropilin. Also, the tumor tissue-penetrating peptide of the present invention allows the removal of heparin binding site, thereby minimizing nonspecific binding.

The antibody having the tumor tissue-penetrating peptide fused therein of the present invention shows a production yield similar to wild-type antibody, and has the property of a bispecific antibody that can target two types of antigens, an antigen to which the antibody binds and neuropilin to which the tumor tissue-penetrating peptide binds. Accordingly, it may allow an antibody to reach a tumor tissue with high efficiency, and thus is expected to have a high effect in treating cancer.

Also, an antibody having the tumor tissue-penetrating peptide fused therein or a fragment thereof maintains the antigen binding capacity which the wild-type antibody originally has, unique function of heavy-chain constant region (Fc), i.e., binding with FcγRn (neonatal Fc receptor) and FcRs (Fc gamma receptors), and accordingly has a long serum half-life. Also, it has an advantage that the binding site (protein A and protein G) during the purification process is preserved, and the antibody-dependent cellular cytotoxicity and complement-dependent cellular cytotoxicity may be maintained.

Also, the tumor tissue-penetrating peptide specifically binds to neuropilin, and competes with VEGF165A binding to neuropilin. Accordingly, it inhibits the angiogenesis function caused by VEGF165A binding to neuropilin, and thus is expected to have an effect of treating both cancer and angiogenesis-related diseases.

The cancer may be selected from the group consisting of squamous cell carcinoma, small cell lung cancer, non-small cell lung cancer, adenocarcinoma of lung, squamous cell carcinoma of lung, peritoneal cancer, skin cancer, skin or ocular melanoma, rectal cancer, anal cancer, esophageal cancer, small intestine cancer, endocrine cancer, parathyroid cancer, adrenal cancer, soft tissue sarcoma, urethral cancer, chronic or acute leukemia, lymphoma, hepatoma, gastrointestinal cancer, pancreatic cancer, glioblastoma, cervical cancer, ovarian cancer, liver cancer, bladder cancer, liver tumor, breast cancer, pancreatic cancer, colon cancer, colorectal cancer, endometrial cancer or uterine cancer, salivary gland cancer, kidney cancer, liver cancer, prostate cancer, vulva cancer, thyroid cancer, liver cancer and head and neck cancer.

The angiogenesis-related disease may be selected from the group consisting of diabetic retinopathy, retinopathy of prematurity, corneal graft rejection, neovascular glaucoma, retrolental fibroplasia, epidemic keratoconjunctivitis, vitamin A deficiency, contact lens overwear, atopic keratitis, superior limbic keratitis, pterygium keratitis sicca, sjogrens, acne rosacea, phylectenulosis, syphilis, mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginalkeratolysis, trauma, rheumatoid arthritis, systemic lupus, polyarteritis, Wegeners sarcoidosis, scleritis, Steven's Johnson disease, periphigoid radial keratotomy, corneal graft rejection, keloid, wound granulation, and glomerulonephritis.

When the composition is prepared as a pharmaceutical composition for preventing or treating cancer or angiogenesis-related diseases, the composition may include a pharmaceutically acceptable carrier. Examples of the pharmaceutically acceptable carrier included in the composition may include, but are not limited to, lactose, dextrose, sucrose, sorbitol, mannitol, starch, acacia rubber, calcium phosphate, alginate, gelatin, calcium silicate, minute crystalline cellulose, polyvinyl pyrrolidone, cellulose, water, syrup, methyl cellulose, methyl hydroxy benzoate, propyl hydroxy benzoate, talc, magnesium stearate and mineral oil, etc., but are not limited thereto. In addition to the above ingredients, the pharmaceutical composition may further include a lubricant, a humectant, a sweetener, a flavoring agent, an emulsifier, a suspension, a preservative, etc.

The pharmaceutical composition for preventing or treating cancer or angiogenesis-related diseases may be administered orally or parenterally. Such a parenteral administration includes intravenous injection, subcutaneous injection, intramuscular injection, intraperitoneal injection, endothelial administration, topical administration, nasal administration, intrapulmonary administration, intrarectal administration, etc. Because a protein or peptide is digested when administered orally, it is preferred that a composition for oral administration is formulated to coat an active substance or to be protected against degradation in stomach. Also, the pharmaceutical composition may be administered by any device which can transport active substances to target cells.

Proper dose of the pharmaceutical composition for preventing or treating cancer or angiogenesis-related diseases may vary according to various factors such as method for formulating, administration method, age, weight, gender, pathological state of patient, food, administration time, administration route, excretion rate and reaction sensitivity, etc. Preferably, a proper dose of the composition is within the range of 0.001 and 100 mg/kg based on an adult. The term "pharmaceutically effective dose" as used herein refers to an amount sufficient to prevent or treat cancer or angiogenesis-related diseases.

The composition may be formulated with pharmaceutically acceptable carriers and/or excipients according to a method that can be easily carried out by those skilled in the art, and may be provided in a unit-dose form or enclosed in a multiple-dose vial. Here, the formulation may be in the form of a solution, a suspension, syrup or an emulsion in oily or aqueous medium, or may be extracts, powders, granules, tablets or capsules, and may further include a dispersion agent or a stabilizer. Also, the composition may be administered individually or in combination with other therapeutic agents, and may be administered sequentially or simultaneously with conventional therapeutic agents. Meanwhile, the composition includes an antibody or an antigen-binding fragment, and thus may be formulated into immuno liposome. Liposome including an antibody may be prepared according to a method well known in the pertinent art. The immuno liposome is a lipid composition including phosphatidylcholine, cholesterol and polyethyleneglycol-derived phosphatidylethanolamine, and may be prepared by reverse phase evaporation method. For example, a Fab' fragment of antibody may be conjugated to liposome through disulphide exchange reaction. Liposome may further include chemical therapeutic agents such as Doxorubicin.

Also, an aspect of the present invention provides a composition for diagnosing cancer, including the tumor tissue-penetrating peptide, or a fusion protein, a small molecule drug, a nanoparticle, or a liposome having the peptide fused therein.

The term "diagnosing" as used herein refers to demonstrating the presence or characteristic of a pathophysiological condition. Diagnosing in the present invention refers to demonstrating the onset and progress of cancer.

The tumor tissue-penetrating peptide may bind to a fluorescent substance for molecular imaging in order to diagnose cancer through images.

The fluorescent substance for molecular imaging refers to all substances generating fluorescence. Preferably, red or near-infrared fluorescence is emitted, and more preferably, a fluorescence with high quantum yield is emitted. However, the fluorescence is not limited thereto.

Preferably, the fluorescent substance for molecular imaging is a fluorescent substance, a fluorescent protein or other substances for imaging, which may bind to the tumor tissue-penetrating peptide, but is not limited thereto.

Preferably, the fluorescent substance is fluorescein, BODYPY, tetramethylrhodamine, Alexa, cyanine, allopicocyanine, or a derivative thereof, but is not limited thereto.

Preferably, the fluorescent protein is Dronpa protein, enhanced green fluorescence protein (EGFP), red fluorescent protein (DsRFP), Cy5.5, which is a cyanine fluorescent substance presenting near-infrared fluorescence, or other fluorescent proteins, but is not limited thereto.

Preferably, other substances for imaging are ferric oxide, radioactive isotope, etc., but are not limited thereto, and they may be applied to imaging equipment such as MR, PET.

What is claimed is:

1. A tumor tissue-penetrating peptide specifically binding to neuropilin, represented by the amino acid sequence selected from the group consisting of SEQ ID NO: 1 to SEQ ID NO: 4.

2. The tumor tissue-penetrating peptide according to claim 1, wherein the peptide further comprises a linker peptide.

3. The tumor tissue-penetrating peptide according to claim 2, wherein the linker peptide consists of 1 to 50 amino acids.

4. The tumor tissue-penetrating peptide according to claim 2, wherein the linker peptide consists of glycine(G), serine(S), or alanine(A).

5. The tumor tissue-penetrating peptide according to claim 2, wherein the linker peptide consists of the amino acid sequence of (GA)n identified by SEQ ID NO: 11 or (GGGGS)m identified by SEQ ID NO: 12, wherein n and m are each independently an integer between 1 and 20.

6. The tumor tissue-penetrating peptide according to claim 2, wherein the tumor tissue-penetrating peptide comprises an amino acid sequence selected from the group consisting of SEQ ID NO: 5 to SEQ ID NO: 10.

7. A fusion protein having the fused tumor tissue-penetrating peptide of claim 1 fused therein.

8. The fusion protein according to claim 7, wherein the protein is selected from the group consisting of antibodies, antibody fragments, immunoglobulin, peptides, enzymes, growth factors, cytokine, transcription factors, toxins, antigen peptides, hormones, carrier proteins, motor function proteins, receptors, signaling proteins, storage proteins, membrane proteins, transmembrane proteins, internal proteins, external proteins, secretory proteins, viral proteins, glycoproteins, cleaved proteins, protein complexes, and chemically modified proteins.

9. The fusion protein according to claim 7, wherein the fusion of tumor tissue-penetrating peptide is mediated by a linker peptide.

10. The fusion protein according to claim 8, wherein said antibody fragments is a heavy-chain constant region (Fc), an antigen binding fragment (Fab), a single chain variable fragment (scFv), a heavy-chain variable region (VH), a light-chain constant region (CL) or a light-chain variable region (VL) of an antibody.

11. The fusion protein according to claim 8, wherein the protein is an antibody and a tumor tissue-penetrating peptide is fused to the C-terminus of the heavy-chain constant region (Fc) of the antibody.

12. The fusion protein according to claim 11, wherein the fusion is mediated by a linker peptide.

13. The fusion protein according to claim 11, wherein the antibody is selected from the group consisting of IgG, IgM, IgA, IgD and IgE.

14. A nanoparticle having the tumor tissue-penetrating peptide of claim 1 fused therein.

15. The nanoparticle according to claim 14, wherein the fusion is mediated by a linker peptide.

16. A liposome having the tumor tissue-penetrating peptide of claim 1 fused therein.

17. The liposome according to claim 16, wherein the fusion is mediated by a linker peptide.

18. A small molecule drug having the tumor tissue-penetrating peptide of claim 1 fused therein.

19. A polynucleotide coding a peptide represented by an amino acid sequence selected from the group consisting of SEQ ID NO: 1 to SEQ ID NO: 10.

20. A composition for treating, preventing or diagnosing cancer or angiogenesis-related diseases, comprising the peptide of claim 1.

21. A composition for treating, preventing or diagnosing cancer or angiogenesis-related diseases, comprising the fusion protein of claim 7.

22. A method for treating or preventing cancer or angiogenesis-related diseases, comprising administering to a subject in need thereof a composition comprising the peptide of claim 1.

23. A method for treating or preventing cancer or angiogenesis-related diseases, comprising administering to a subject in need thereof a composition comprising the fusion protein of claim 7.

24. A composition for treating, preventing or diagnosing cancer or angiogenesis-related diseases, comprising the nanoparticle of claim 14.

25. A composition for treating, preventing or diagnosing cancer or angiogenesis-related diseases, comprising the liposome of claim 16.

26. A composition for treating, preventing or diagnosing cancer or angiogenesis-related diseases, comprising the small molecule drug of claim 18.

27. A method for treating or preventing cancer or angiogenesis-related diseases, comprising administering to a subject in need thereof a composition comprising the nanoparticle of claim 14.

28. A method for treating or preventing cancer or angiogenesis-related diseases, comprising administering to a subject in need thereof a composition comprising the liposome of claim 16.

29. A method for treating or preventing cancer or angiogenesis-related diseases, comprising administering to a subject in need thereof a composition comprising the small molecule drug of claim 18.

* * * * *